US011925436B2

(12) United States Patent
Yamamoto et al.

(10) Patent No.: US 11,925,436 B2
(45) Date of Patent: *Mar. 12, 2024

(54) ACOUSTIC WAVE DEVICE AND CONTROL METHOD OF ACOUSTIC WAVE DEVICE

(71) Applicant: FUJIFILM Corporation, Tokyo (JP)

(72) Inventors: Katsuya Yamamoto, Kanagawa (JP); Tomoki Inoue, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 924 days.

This patent is subject to a terminal disclaimer.

(21) Appl. No.: 16/918,662

(22) Filed: Jul. 1, 2020

(65) Prior Publication Data

US 2020/0329973 A1 Oct. 22, 2020

Related U.S. Application Data

(63) Continuation of application No. PCT/JP2018/046191, filed on Dec. 14, 2018.

(30) Foreign Application Priority Data

Jan. 31, 2018 (JP) .................................. 2018-015331

(51) Int. Cl.
*A61B 5/00* (2006.01)
*G06T 11/00* (2006.01)
(Continued)

(52) U.S. Cl.
CPC .......... *A61B 5/0093* (2013.01); *A61B 5/6848* (2013.01); *A61B 5/7425* (2013.01);
(Continued)

(58) Field of Classification Search
CPC ... A61B 5/0093; A61B 5/6848; A61B 5/7425; A61B 5/14503; A61B 5/14532;
(Continued)

(56) References Cited

U.S. PATENT DOCUMENTS

2016/0135689 A1\* 5/2016 Murakoshi ........... A61B 5/0095
600/407
2016/0165127 A1 6/2016 Naruse et al.

FOREIGN PATENT DOCUMENTS

| JP | 2016064011 A | 4/2016 |
| JP | 2017169786 A | 9/2017 |
| WO | 2015/015932 A1 | 2/2015 |

OTHER PUBLICATIONS

An Office Action; "Notice of Reasons for Refusal," mailed by the Japanese Patent Office dated Jan. 11, 2022, which corresponds to Japanese Patent Application No. 2019-568921 and is related to U.S. Appl. No. 16/918,662 with with English translation.
(Continued)

*Primary Examiner* — Peter Luong

(74) *Attorney, Agent, or Firm* — Studebaker & Brackett PC

(57) ABSTRACT

An acoustic wave device includes: an insertion object having a photoacoustic wave generator; an insertion object image signal generator that generates an insertion object image signal from a reception signal of an acoustic wave from the photoacoustic wave generator; a first signal width detector that detects a first signal width of a portion of a predetermined signal strength in the insertion object image signal; and an insertion object display image signal generator that generates, in a case where the first signal width is larger than a second signal width, an insertion object display image signal of a width having a center at a peak position of the insertion object image signal and corresponding to the second signal width, and generates, in a case where the first signal width is smaller than the second signal width, an insertion object display image signal having a width smaller than the second signal width.

21 Claims, 19 Drawing Sheets

(51) Int. Cl.
    *G16H 20/40*     (2018.01)
    *G16H 30/40*     (2018.01)
    *A61B 5/145*     (2006.01)

(52) U.S. Cl.
    CPC .......... *G06T 11/001* (2013.01); *G06T 11/008* (2013.01); *G16H 20/40* (2018.01); *G16H 30/40* (2018.01); *A61B 5/14503* (2013.01); *A61B 5/14532* (2013.01); *G06T 2200/24* (2013.01)

(58) Field of Classification Search
    CPC ........... A61B 8/12; A61B 8/14; G06T 11/001; G06T 11/008; G06T 2200/24; G16H 20/40; G16H 30/40; G16H 40/63
    See application file for complete search history.

(56) References Cited

OTHER PUBLICATIONS

International Search Report issued in PCT/JP2018/046191; dated Feb. 12, 2019.
International Preliminary Report On Patentability and Written Opinion issued in PCT/JP2018/046191; dated Aug. 4, 2020.
An Office Action; "Notice of Reasons for Refusal," mailed by the Japanese Patent Office dated Jul. 13, 2021, which corresponds to Japanese Patent Application No. 2019-568921 and is related to U.S. Appl. No. 16/918,662 with with English translation.

* cited by examiner

ACOUSTIC WAVE DEVICE AND CONTROL METHOD OF ACOUSTIC WAVE DEVICE

CROSS-REFERENCE TO RELATED APPLICATIONS

This application is a Continuation of PCT International Application No. PCT/JP2018/046191 filed on Dec. 14, 2018, which claims priority under 35 U.S.C § 119(a) to Japanese Patent Application No. 2018-015331 filed on Jan. 31, 2018. Each of the above application(s) is hereby expressly incorporated by reference, in its entirety, into the present application.

BACKGROUND OF THE INVENTION

1. Field of the Invention

The present invention relates to an acoustic wave device and a control method of the acoustic wave device, and more particularly, to an acoustic wave device including an insertion object such as a puncture needle and a control method of the acoustic wave device.

2. Description of the Related Art

In the related art, a technique for obtaining a tomographic image of a subject using acoustic waves such as ultrasonic waves and photoacoustic waves is known. For example, an ultrasonic wave device that obtains a tomographic image of a subject using ultrasonic waves generally transmits an ultrasonic beam from an array transducer in which a plurality of elements are arranged toward the inside of the subject, and receives ultrasonic echoes from the subject using the array transducer to acquire element data. Further, the ultrasonic wave device may electrically process the acquired element data to generate an ultrasonic image in which a portion of the subject is included. Further, for example, a photoacoustic wave device that obtains a tomographic image of a subject using photoacoustic waves generally irradiates the inside of the subject with laser beam emitted from a laser light source, and receives photoacoustic waves emitted from an in-vivo substance such as hemoglobin included in a tissue of the subject using an array transducer to acquire element data. The photoacoustic wave device may electrically process the element data to generate a photoacoustic image in which a portion of the subject is included.

Further, in the related art, a technique for performing treatments such as sampling and injection of a drug solution by inserting an insertion object such as a puncture needle into a subject has been used. In a case where the treatments such as the sampling and the injection of the drug solution are performed using the insertion object in this way, for safety of the subject, various measures capable of confirming a position of a distal end portion of the insertion object have been devised.

For example, JP2016-064011A discloses an ultrasonic wave device that is provided with a puncture needle having a photoacoustic wave generator at a distal end portion thereof, irradiates the photoacoustic wave generator with laser beam, and receives generated photoacoustic waves to generate an image of the distal end portion of the puncture needle. The ultrasonic wave device disclosed in JP2016-064011A displays a composite image in which the image of the distal end portion of the puncture needle is superimposed on a tomographic image of the subject generated using ultrasonic waves on a display.

SUMMARY OF THE INVENTION

However, according to reviews of the present inventors, for example, in a case where an insertion object such as a puncture needle having a photoacoustic wave generator at a distal end portion thereof, as disclosed in JP2016-064011A, is inserted into a blood vessel, there is a concern that a so-called artifact may occur in which an image of the distal end portion of the insertion object is expanded and displayed. In such a case, there is a problem in that a user cannot easily recognize a tissue or the like included in a tomographic image of a subject due to the presence of the artifact, and thus, it is difficult for the user to confirm an accurate position of the distal end portion of the insertion object.

The present invention has been made in order to solve such a related-art problem, and an object of the present invention is to provide an acoustic wave device and a control method of the acoustic wave device capable of preventing a situation where a tissue or the like of a subject included in an acoustic wave image is not easily visually recognized by a user due to the presence of an artifact.

In order to achieve the above object, according to an aspect of the present invention, there is provided an acoustic wave device including: a subject beam irradiator that irradiates an inside of a subject with an ultrasonic beam or laser beam to cause an acoustic wave to be emitted from a tissue of the subject; an insertion object that is able to be inserted into the subject and has a photoacoustic wave generator at a distal end portion thereof; an insertion object laser light source that irradiates the photoacoustic wave generator of the insertion object with laser beam to generate a photoacoustic wave from the photoacoustic wave generator; a reception signal generator that receives the acoustic wave emitted from the tissue of the subject to generate a tomographic image generating reception signal, and receives the photoacoustic wave from the photoacoustic wave generator to generate an insertion object image generating reception signal; a tomographic image signal generator that generates a tomographic image signal that represents a tomographic image of the subject from the tomographic image generating reception signal; an insertion object image signal generator that generates an insertion object image signal that represents an image of the distal end portion of the insertion object from the insertion object image generating reception signal; a first signal width detector that detects a first signal width of the insertion object image signal having a signal strength of a predetermined ratio to a peak value of a signal strength in the insertion object image signal; an insertion object display image signal generator that generates, in a case where the first signal width is larger than a predetermined second signal width, an insertion object display image signal having a center at a peak position where the signal strength of the insertion object image signal becomes the peak value and having a maximum width corresponding to the second signal width from the insertion object image signal, and generates, in a case where the first signal width is smaller than the second signal width, an insertion object display image signal having a center at the peak position and having a maximum width smaller than the second signal width from the insertion object image signal; and a display, wherein the acoustic wave device superimposes the tomographic image of the subject and the image of the distal end portion of the insertion object to be displayed on the display on the basis of the tomographic image signal and the insertion object display image signal.

Further, in a case where the first signal width is larger than the second signal width, the insertion object display image signal generator may generate the insertion object display image signal having the center at the peak position and formed by a portion ranging from the center to the second signal width, in the insertion object image signal.

Further, in a case where the first signal width is smaller than the second signal width, the insertion object display image signal generator may generate the insertion object display image signal having a center at the peak position and formed by a portion ranging from the center to the first signal width, in the insertion object image signal.

Further, in a case where the first signal width is smaller than a third signal width predetermined as a value smaller than the second signal width, the insertion object display image signal generator may generate the insertion object display image signal having a center at the peak position and having a maximum width corresponding to the third signal width.

Further, the insertion object display image signal generator may generate an enlarged image signal obtained by enlarging the insertion object image signal until the signal width having the signal strength of the predetermined ratio to the peak value becomes larger than the third signal width, and may generate a portion having a center at the peak position and ranging from the center to the third signal width, in the enlarged image signal, as the insertion object display image signal.

Further, it is preferable that the enlarged image signal is an image signal obtained by increasing a signal strength of at least the portion having the center at the peak position and ranging from the center to the third signal width in the insertion object image signal at a predetermined magnification.

Further, the enlarged image signal may be an image signal obtained by enlarging a signal width of at least a portion including a signal strength larger than the signal strength of the predetermined ratio in the insertion object image signal to the peak value at a predetermined magnification.

Further, the enlarged image signal may be an image signal obtained by increasing a signal strength of at least the portion having the center at the peak position and ranging from the center to the third signal width in the insertion object image signal by a predetermined offset amount.

Further, the enlarged image signal may be an image signal obtained by increasing a signal strength of at least a portion smaller than a predetermined signal strength, in the portion having the center at the peak position and ranging from the center to the third signal width in the insertion object image signal, up to the predetermined signal strength.

Further, the enlarged image signal may be an image signal obtained by increasing the signal strength of at least the portion having the center at the peak position and ranging from the center to the third signal width in the insertion object image signal up to the peak value.

The acoustic wave device may further include an image highlighting unit that highlights and displays the image of the distal end portion of the insertion object on the display in a case where the maximum width of the insertion object display image signal is different from the first signal width.

The image highlighting unit may superimpose an outline of a region having a center at the peak position and having the first signal width and the image of the distal end portion of the insertion object to be displayed on the display.

Further, the image highlighting unit may display an outer peripheral portion of the image of the distal end portion of the insertion object in different colors on the display between a case where the maximum width of the insertion object display image signal is larger than the first signal width and a case where the maximum width of the insertion object display image signal is smaller than the first signal width.

Further, the image highlighting unit may display the image of the distal end portion of the insertion object in different colors on the display between a case where the maximum width of the insertion object display image signal is the first signal width and a case where the maximum width of the insertion object display image signal is different from the first signal width.

Further, the image highlighting unit may display the image of the distal end portion of the insertion object in different colors on the display between a case where the maximum width of the insertion object display image signal is larger than the first signal width and a case where the maximum width of the insertion object display image signal is smaller than the first signal width.

An operating unit for the user to perform an input operation and a second signal width setting unit for setting the second signal width are further provided, and the second signal width setting unit is set by the user via the operating unit. The value can be set as the second signal width.

Further, the acoustic wave device may further include: a second signal width setting unit that sets the second signal width; and a distal end diameter reader that reads a diameter of the distal end portion of the insertion object, in which the second signal width setting unit may calculate a converted value by multiplying the diameter of the distal end portion of the insertion object read by the distal end diameter reader by a predetermined coefficient, and sets the converted value as the second signal width.

The acoustic wave device may further include a second signal width setting unit that sets the second signal width, in which the second signal width setting unit may set the second signal width on the basis of the first signal width detected in a calibration medium.

Further, the subject beam irradiator may irradiate the inside of the subject with an ultrasonic beam to cause an ultrasonic echo to be emitted from the tissue of the subject, and the reception signal generator may receive the ultrasonic echo from the tissue of the subject to generate the tomographic image generating signal.

Alternatively, the subject beam irradiator may irradiate the inside of the subject with laser beam to cause the photoacoustic wave to be emitted from the tissue of the subject, and the reception signal generator may receive the photoacoustic wave from the tissue of the subject to generate the tomographic image generating reception signal.

According to another aspect of the present invention, there is provided a control method of an acoustic wave device, the method including: receiving an acoustic wave emitted from a tissue of a subject by irradiating the inside of the subject with an ultrasonic beam or laser beam to generate a tomographic image generating reception signal; irradiating a photoacoustic wave generator of an insertion object with the laser beam, the insertion object being able to be inserted into the subject and having the photoacoustic wave generator at a distal end portion; receiving a photoacoustic wave from the photoacoustic wave generator to generate an insertion object image generating reception signal; generating an insertion object image signal representing an image of the distal end portion of the insertion object from the insertion object image generating reception signal; generating a tomographic image signal that represents a tomographic image of the subject from the tomographic image generating reception signal; detecting a first signal width of the insertion object image signal having a signal strength of a predetermined ratio to a peak value of the signal strength in the insertion object image signal; generating, in a case where the first signal width is larger than a predetermined second signal width, an insertion object display image signal having a center at a peak position where the signal strength of the insertion object image becomes the peak value and having a maximum width corresponding to the second signal width, from the insertion object image signal; generating, in a case where the first signal width is smaller than the second signal width, an insertion object display image signal having a center at the peak position and having a maximum width smaller than the second signal width; and superimposing a tomographic image of the subject and an image of the distal end portion of the insertion object to be displayed on a display on the basis of the tomographic image signal and the insertion object display image signal.

According to the present invention, since there are provided the first signal width detector that detects a first signal width of an insertion object image signal having a signal strength of a predetermined ratio to a peak value of a signal strength in the insertion object image signal; and an insertion object display image signal generator that generates, in a case where the first signal width is larger than a predetermined second signal width, an insertion object display image signal having a center at a peak position where the signal strength of the insertion object image becomes the peak value and having a maximum width corresponding to the second signal width from the insertion object image signal and generates, in a case where the first signal width is smaller than the second signal width, an insertion object display image signal having a center at the peak position and having a maximum width smaller than the second signal width from the insertion object image signal, it is possible to prevent a situation where an acoustic wave image is not easily visually recognized due to the presence of an artifact.

DESCRIPTION OF THE PREFERRED EMBODIMENTS

Hereinafter, embodiments of the present invention will be described with reference to the accompanying drawings.

First Embodiment

Figure 1:
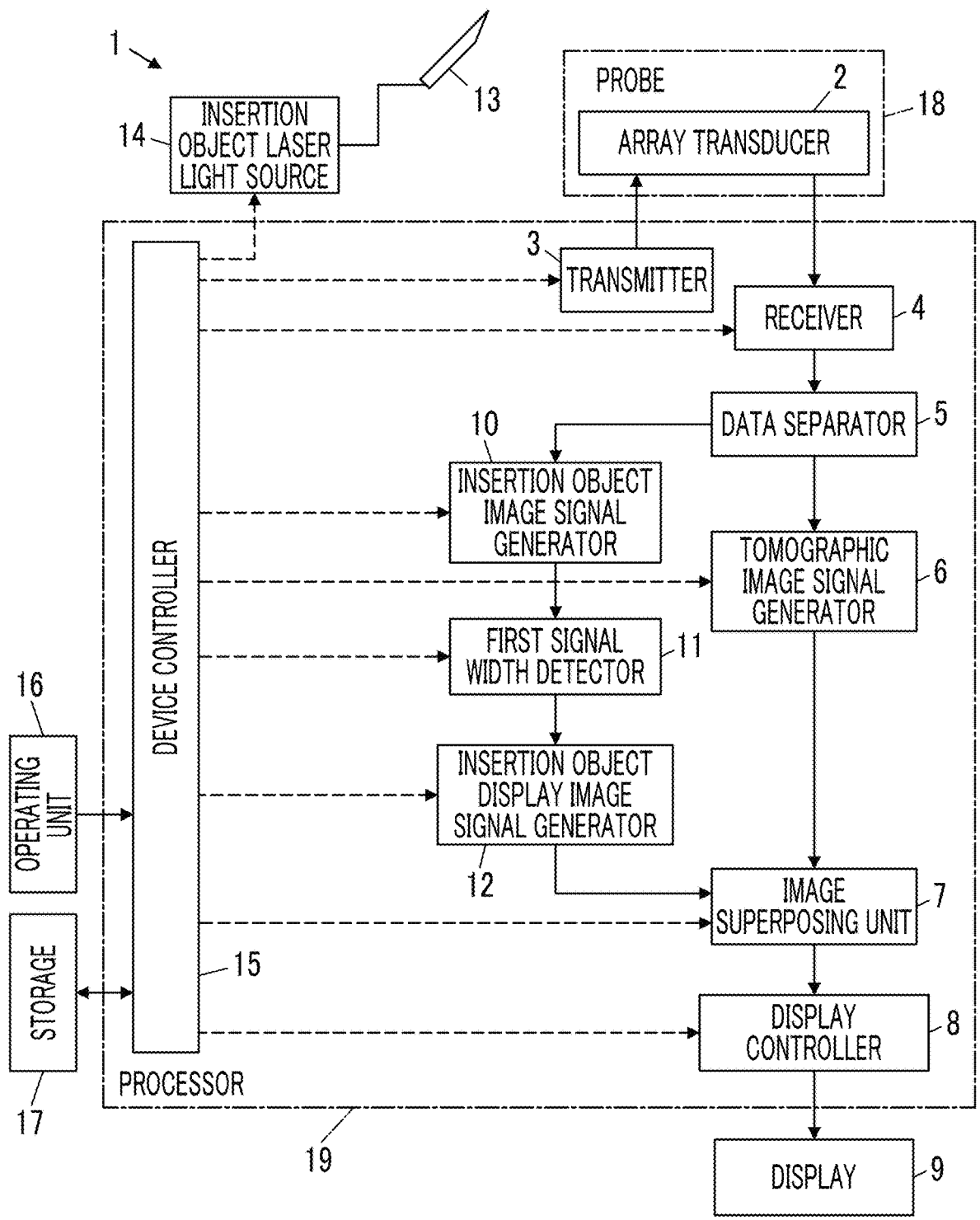
FIG. 1 is a block diagram showing a configuration of an ultrasonic wave device according to a first embodiment of the present invention.

FIG. 1 shows a configuration of an ultrasonic wave device 1 that is an acoustic wave device according to a first embodiment of the present invention. As shown in FIG. 1, the ultrasonic wave device 1 includes an array transducer 2, and a transmitter 3 and a receiver 4 are respectively connected to the array transducer 2. A data separator 5, a tomographic image signal generator 6, an image superposing unit 7, a display controller 8, and a display 9 are sequentially connected to the receiver 4. Further, an insertion object image signal generator 10 is connected to the data separator 5. Further, a first signal width detector 11 and an insertion object display image signal generator 12 are sequentially connected to the insertion object image signal generator 10. Further, the insertion object display image signal generator 12 is connected to the image superposing unit 7. In addition, the ultrasonic wave device 1 includes an insertion object 13, and the insertion object 13 is connected to an insertion object laser light source 14.

Further, a device controller 15 is connected to the transmitter 3, the receiver 4, the tomographic image signal generator 6, the image superposing unit 7, the display controller 8, the insertion object image signal generator 10, the first signal width detector 11, the insertion object display image signal generator 12, and the insertion object laser light source 14, and an operating unit 16 and a storage 17 are connected to the device controller 15. The device controller 15 and the storage 17 are connected to each other so that bidirectional information exchange can be performed.

The array transducer 2 is included in a probe 18, and a processor 19 is configured by the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15.

Figure 2:
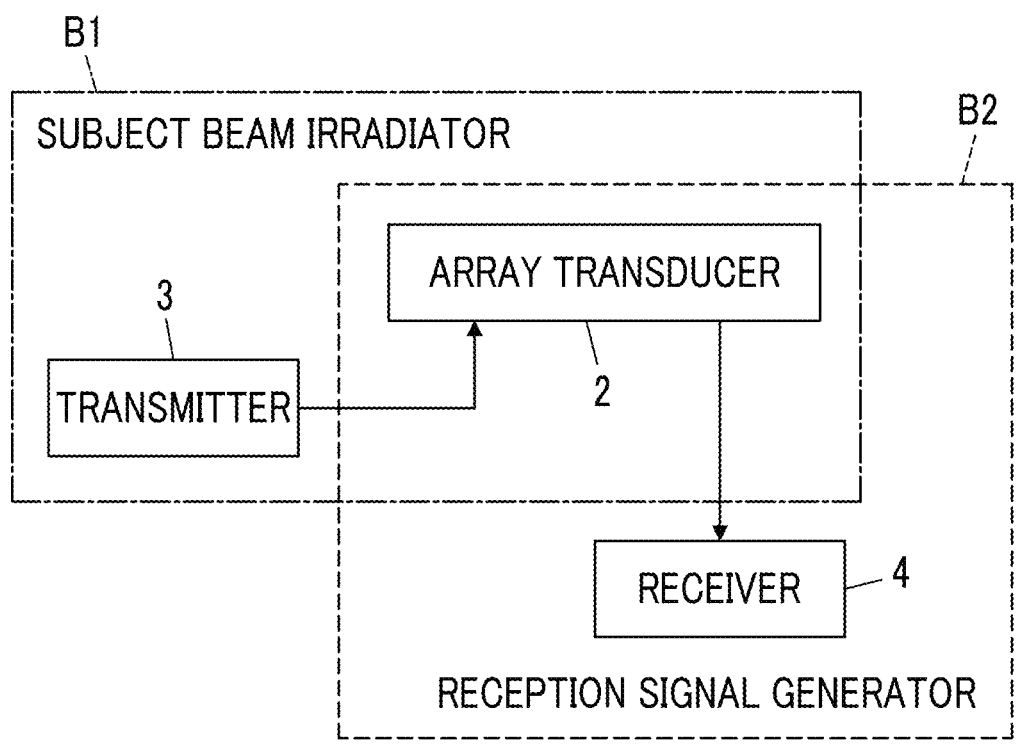
FIG. 2 is a block diagram showing an internal configuration of a subject beam irradiator and a reception signal generator according to the first embodiment of the present invention.

As shown in FIG. 2, a subject beam irradiator B1 is configured by the array transducer 2 and the transmitter 3, and a reception signal generator B2 is configured by the array transducer 2 and the receiver 4.

Figure 3:
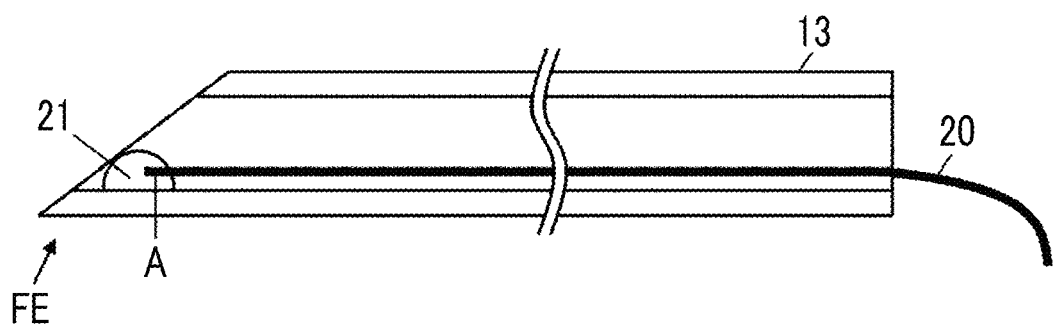
FIG. 3 is a diagram showing an example of an insertion object according to the first embodiment of the present invention.

An insertion object 13 shown in FIG. 1 is inserted into a subject in a case where ultrasonic diagnosis is performed, and is used for performing treatments such as sampling and injection of a drug solution. As the insertion object 13, for example, a puncture needle, a catheter, forceps, or the like may be used, but a puncture needle as shown in FIG. 3 may be used, for example. Inside the insertion object 13 shown in FIG. 3, a light guide member 20 such as an optical fiber is provided so as to extend from the insertion object laser light source 14 disposed outside to the vicinity of a distal end portion FE of the insertion object 13. Further, inside the insertion object 13, a photoacoustic wave generator 21 is disposed in the vicinity of the distal end portion FE of the insertion object 13, and a distal end portion A of the light guide member 20 is embedded in the photoacoustic wave generator 21.

The photoacoustic wave generator 21 is made of a material that absorbs light, for example, a synthetic resin such as an epoxy resin, a fluorine resin, or a polyurethane resin mixed with a black pigment, and contracts and expands according to irradiation of light to generate photoacoustic waves. In the insertion object 13 shown in FIG. 3, as light emitted from the insertion object laser light source 14 is applied to the photoacoustic wave generator 21 via the light guide member 20, photoacoustic waves are generated from the photoacoustic wave generator 21.

Figure 4:
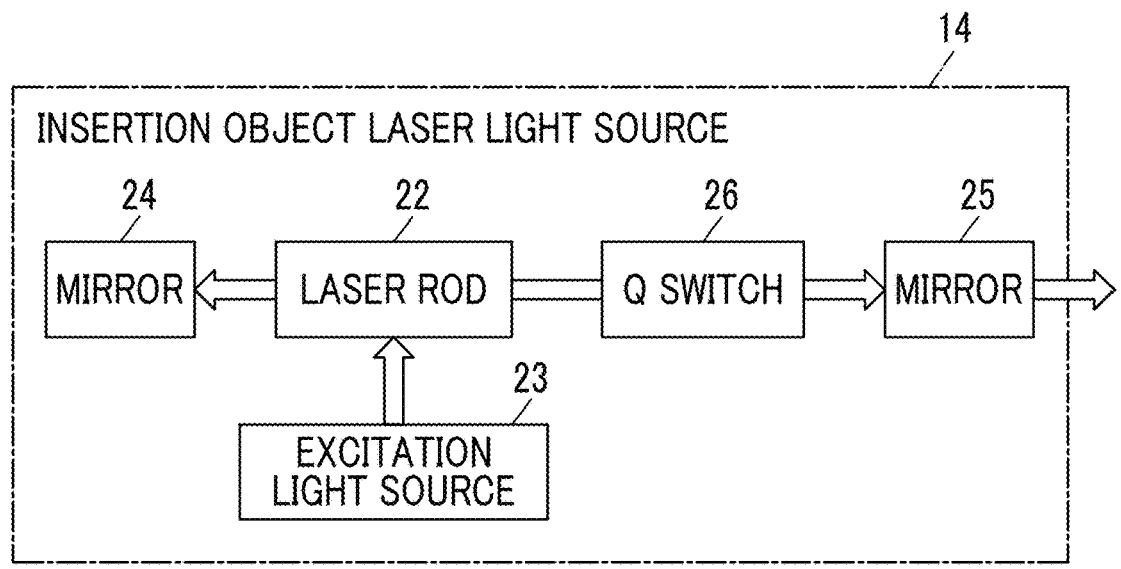
FIG. 4 is a block diagram showing an internal configuration of an insertion object laser light source according to the first embodiment of the present invention.

The insertion object laser light source 14 includes a laser rod 22, an excitation light source 23, a mirror 24, a mirror 25, and a Q switch 26, as shown in FIG. 4. The laser rod 22 is a laser medium, and for example, an alexandrite crystal may be used as the laser rod 22. The excitation light source 23 is a light source that irradiates the laser rod 22 with excitation light, and for example, a light source such as a flash lamp and a laser diode may be used as the excitation light source 23.

The mirrors 24 and 25 face each other with the laser rod 22 being interposed therebetween, and the mirrors 24 and 25 form an optical resonator. In this optical resonator, the mirror 25 is disposed on the output side. The Q switch 26 is inserted in the optical resonator, in which the Q switch 26 rapidly changes the state of the optical resonator from a state where an insertion loss is large to a state where the insertion loss is small, to thereby make it possible to obtain pulsed laser beam. The pulsed laser beam emitted from the mirror 25 on the output side of the insertion object laser light source 14 is guided to the insertion object 13 through the light guide member 20.

The array transducer 2 of the probe 18 shown in FIG. 1 has a plurality of transducers arranged one-dimensionally or two-dimensionally. Each of these transducers transmits an ultrasonic wave in accordance with a drive signal supplied from the transmitter 3, receives an ultrasonic echo from a subject, and outputs a tomographic image generating reception signal. Further, these elements receive a photoacoustic wave generated by irradiating the photoacoustic wave generator 21 of the insertion object 13 with light from the insertion object laser light source 14, and output an insertion object image generating reception signal.

Each transducer is formed by forming electrodes at both ends of a piezoelectric body made of, for example, a piezoelectric ceramic represented by lead zirconate titanate (PZT), a polymer piezoelectric element represented by polyvinylidene fluoride (PVDF: poly vinylidene di fluoride), a piezoelectric single crystal represented by lead magnesium niobate-lead titanate (PMN-PT: solid solution of lead magnesium niobate-lead titanate), or the like.

The transmitter 3 of the processor 19 includes, for example, a plurality of pulse generators, and supplies each drive signal to the plurality of transducers with an adjusted delay so that the ultrasonic waves transmitted from the plurality of transducers of the array transducer 2 form an ultrasonic beam on the basis of a transmission delay pattern selected according to a control signal from the device controller 15. As described above, in a case where a pulsed voltage or a continuous wave voltage is applied to the electrodes of the transducer of the array transducer 2, the piezoelectric body expands and contracts, and a pulsed ultrasonic wave or a continuous ultrasonic wave is generated from each transducer, and an ultrasonic beam is formed from a composite wave of such ultrasonic waves.

The transmitted ultrasonic beam is reflected by a target such as a portion of a subject, and propagates toward the array transducer 2 of the probe 18. The ultrasonic echo that propagates toward the array transducer 2 is received by each transducer that forms the array transducer 2. Here, each transducer that forms the array transducer 2 expands and contracts according to the reception of the propagating ultrasonic echo to generate an electric signal, and output the electric signal to the receiver 4 as a tomographic image generating reception signal.

Further, the photoacoustic wave generated by irradiating the photoacoustic wave generator 21 of the insertion object 13 with light emitted from the insertion object laser light source 14 is also received by each transducer that forms the array transducer 2. Here, each transducer that forms the array transducer 2 expands and contracts according to the reception of the photoacoustic wave, in a similar way to the reception of the ultrasonic wave, to generate an electric signal, and outputs the electric signal to the receiver 4 as an insertion object image generating reception signal.

Figure 5:
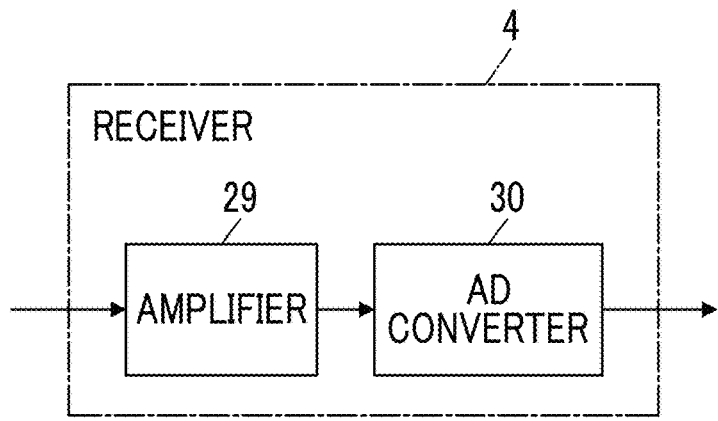
FIG. 5 is a block diagram showing an internal configuration of a receiver according to the first embodiment of the present invention.

The receiver 4 of the processor 19 processes the tomographic image generating reception signal and the insertion object image generating reception signal output from the array transducer 2 according to a control signal from the device controller 15. As shown in FIG. 5, the receiver 4 has a configuration in which an amplifier 29 and an analog digital (AD) converter 30 are connected in series. The amplifier 29 amplifies the tomographic image generating reception signal and the insertion object image generating reception signal input from each of the elements that form the array transducer 2, and transmits the amplified reception signals to the AD converter 30. The AD converter 30 converts the tomographic image generating reception signal and the insertion object image generating reception signal transmitted from the amplifier 29 into digitized data, respectively, and transmits the data to the data separator 5 of the processor 19.

The data separator 5 of the processor 19 separates the data of the tomographic image generating reception signal output from the receiver 4 from the data of the insertion object image generating reception signal, outputs the data of the tomographic image generating reception signal to the tomographic image signal generator 6, and outputs the data of the insertion object image generating reception signal to the insertion object image signal generator 10.

Figure 6:
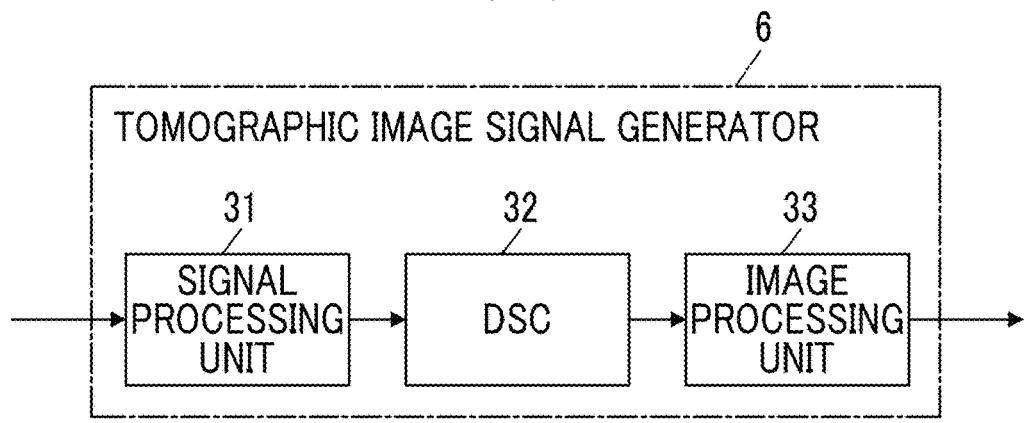
FIG. 6 is a block diagram showing an internal configuration of a tomographic image signal generator according to the first embodiment of the present invention.

As shown in FIG. 6, the tomographic image signal generator 6 of the processor 19 has a configuration in which a signal processing unit 31, a digital scan converter (DSC) 32, and an image processing unit 33 are connected in series. The signal processing unit 31 performs a reception focus process of giving each delay to each piece of data of the tomographic image generating reception signal on the basis of a reception delay pattern selected according to a control signal from the device controller 15 and performing addition (phasing addition). By the reception focus process, a sound ray signal in which a focus of an ultrasonic echo is narrowed to one scan line is generated. In addition, the signal processing unit 31 corrects attenuation due to a propagation distance according to the depth of a position where an ultrasonic wave is reflected for the generated sound ray signal, and then, performs an envelope detection process to generate a B-mode image signal that is tomographic image information on a tissue inside the subject. The B-mode image signal generated in this way is output to the DSC 32.

The DSC 32 of the tomographic image signal generator 6 raster-converts the B-mode image signal into an image signal according to a normal television signal scanning method. The image processing unit 33 of the tomographic image signal generator 6 performs a variety of necessary image processing such as brightness correction, gradation correction, sharpness correction, and color correction for the image data obtained by the DSC 32, and then, outputs the B-mode image signal to the image superposing unit 7.

The insertion object image signal generator 10 of the processor 19 generates an insertion object image signal that represents an image of the distal end portion FE of the insertion object 13 from the insertion object image generating reception signal. Although not shown, the insertion object image signal generator 10 has the same internal configuration as in the tomographic image signal generator 6. In a case where an insertion object image generating reception signal is input from the data separator 5 to the insertion object image signal generator 10, the insertion object image signal generator 10 performs the same process as the process performed by the tomographic image signal generator 6 for the insertion object image generating reception signal, and generates an insertion object image signal that represents an image of the distal end portion FE of the insertion object 13.

The first signal width detector 11 of the processor 19 detects a first signal width of an insertion object image signal having a signal strength of a predetermined ratio to a peak value of a signal strength in the insertion object image signal generated by the insertion object image signal generator 10. The first signal width refers to the width of a signal group having the signal strength of the predetermined ratio to the peak value of the signal strength in the insertion object image signal generated by the insertion object image signal generator 10. For example, in a case where the predetermined ratio is set to 20%, the first signal width detector 11 detects a signal width of an insertion object image signal having a value of 20% of the peak value of the signal strength of the insertion object image signal, as the first signal width.

However, in a case where the distal end portion FE of the insertion object 13 is inserted into a blood vessel or the like, a photoacoustic wave that propagates around the distal end portion FE of the insertion object 13 may not be easily attenuated. Accordingly, for example, in a case where the distal end portion FE of the insertion object 13 is inserted into the blood vessel, an insertion object image signal having a high signal strength may be obtained in a wide range centering around the peak value, compared with a typical insertion object image signal in a case where the distal end portion FE of the insertion object 13 is not inserted into the blood vessel, for example. In a case where such an insertion object image signal is displayed on the display 9, a so-called artifact is generated in which the image of the distal end portion FE of the insertion object 13 is displayed in an expanded state. The insertion object display image signal generator 12 of the processor 19 generates an insertion object display image signal in which the signal width of the insertion object image signal is adjusted to be equal to or less than a predetermined second signal width in order to prevent such an artifact from being displayed on the display 9.

Here, the insertion object display image signal generator 12 adjusts the signal width of the insertion object image signal on the basis of the first signal width of the insertion object image signal detected by the first signal width detector 11 and the predetermined second signal width.

Here, it is desirable that the second signal width is a signal width set as an upper limit value with respect to a maximum width of the image of the distal end portion FE of the insertion object 13 so that a tomographic image of a subject on which the image of the distal end portion FE of the insertion object 13 is superimposed is easily visually recognized.

The image superposing unit 7 of the processor 19 superimposes the tomographic image of the subject and the image of the distal end portion FE of the insertion object 13 on the basis of the tomographic image signal generated by the tomographic image signal generator 6 and the insertion object display image signal generated by the insertion object display image signal generator 12, and outputs the result to the display controller 8. Here, the "superimposition of the tomographic image of the subject and the image of the distal end portion FE of the insertion object 13" means simple superimposition of the tomographic image of the subject generated on the basis of the tomographic image signal and the image of the distal end portion FE of the insertion object 13 generated on the basis of the insertion object display image signal, or generation of one image in which the tomographic image of the subject and the image of the distal end portion FE of the insertion object 13 are superimposed by forming a composite signal obtained by combining the tomographic image signal and the insertion object display image signal.

The device controller 15 of the processor 19 controls each unit of the ultrasonic wave device 1 on the basis of a program stored in advance in the storage 17 or the like and a user operation through the operating unit 16.

The display controller 8 of the processor 19 performs predetermined processing for an image output from the image superposing unit 7 under the control of the device controller 15 to generate an image that can be displayed on the display 9.

The display 9 of the ultrasonic wave device 1 displays an image generated by the display controller 8, and includes a display device such as a liquid crystal display (LCD).

The operating unit 16 of the ultrasonic wave device 1 is a unit through which a user performs an input operation, and may be configured to include a keyboard, a mouse, a trackball, a touch pad, a touch panel, and the like.

The storage 17 stores an operation program and the like of the ultrasonic wave device 1, and may be configured by a recording medium such as a hard disc drive (HDD), a solid state drive (SSD), a flexible disc (FD), a magneto-optical (MO) disc, a magnetic (MT) tape, a random access memory (RAM), a compact disc (CD), a digital versatile disc (DVD), a secure digital (SD) card or a universal serial bus (USB) memory, a server connected to a network, or the like.

The processor 19 including the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15 may be configured by a central processing unit (CPU), and a control program for causing the CPU to execute various processes, but may be configured using a digital circuit. Further, the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15 may be partially or wholly integrated into one CPU.

Figure 7:
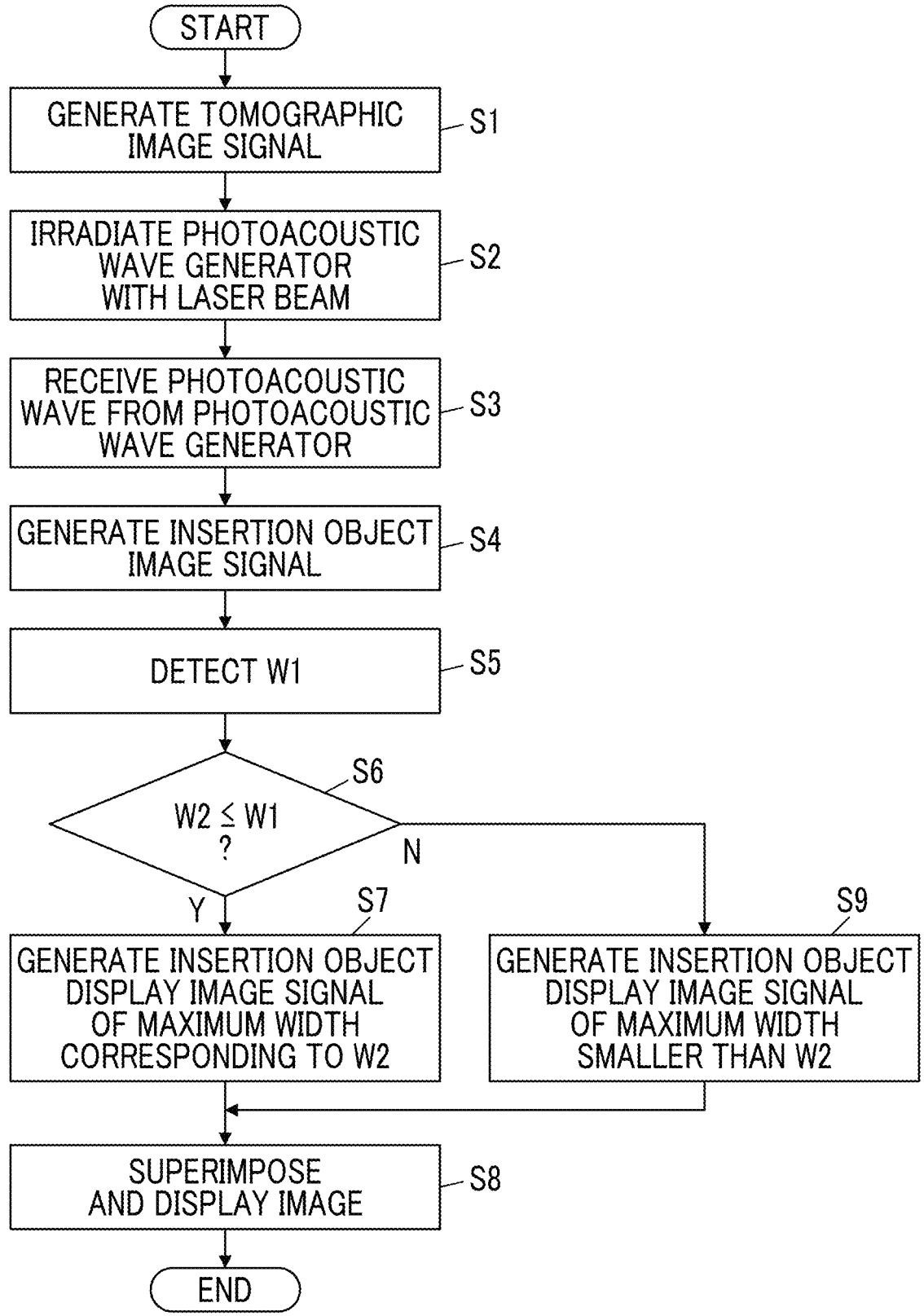
FIG. 7 is a flowchart showing an operation of the ultrasonic wave device according to the first embodiment of the present invention.

Next, an operation of the ultrasonic wave device 1 according to the first embodiment will be described in detail with reference to a flowchart shown in FIG. 7.

First, in step S1, a tomographic image signal that represents a tomographic image of a subject is generated. Here, first, an ultrasonic echo is emitted from a tissue of the subject by irradiating the inside of the subject with an ultrasonic beam from the array transducer 2, and then, the ultrasonic echo is received by the array transducer 2, so that a tomographic image generating reception signal is generated. The tomographic image signal generator 6 generates a tomographic image signal on the basis of the tomographic image generating reception signal obtained in this way.

Next, in step S2, laser beam is applied to the photoacoustic wave generator 21 of the insertion object 13 from the insertion object laser light source 14. Thus, a photoacoustic wave is generated from the photoacoustic wave generator 21.

In the following step S3, the array transducer 2 receives the photoacoustic wave from the photoacoustic wave generator 21, and generates an insertion object image generating reception signal.

In step S4, the insertion object image generating reception signal is output to the insertion object image signal generator 10 through the data separator 5, and an insertion object image signal is generated by the insertion object image signal generator 10.

Figure 8:
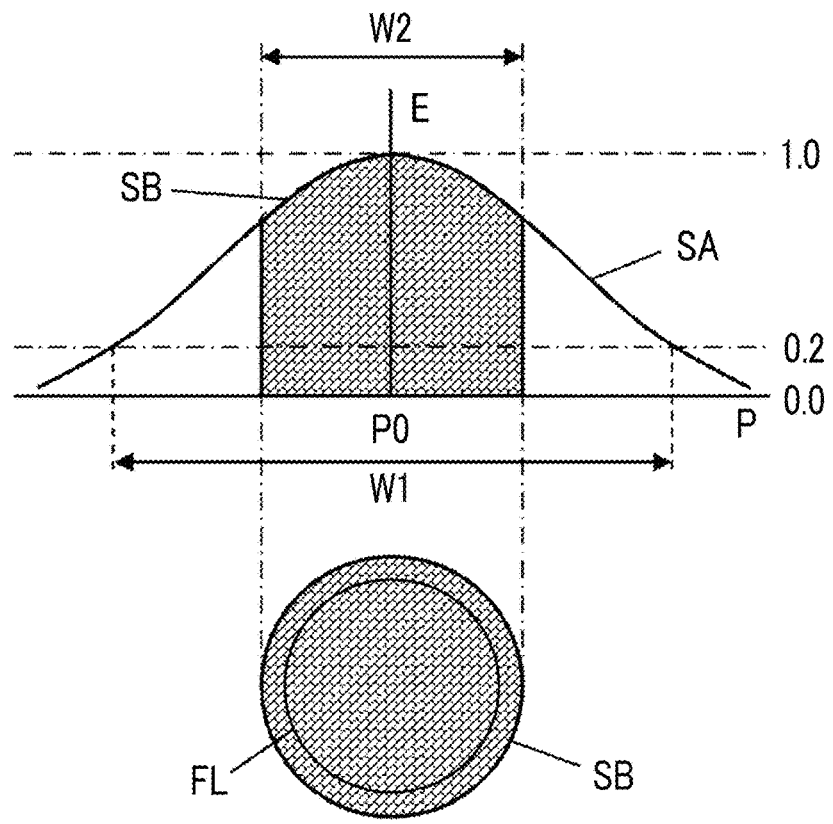
FIG. 8 is a conceptual diagram showing an insertion object display image signal in a case where a first signal width of an insertion object image signal is larger than a second signal width in the first embodiment of the present invention.

In the following step S5, the first signal width detector 11 detects a first signal width of the insertion object image signal generated in step S4. Here, the first signal width detector 11 detects, as the first signal width, a signal width of an insertion object image signal having a signal strength of a predetermined ratio to a peak value of the insertion object image signal. For example, in a case where the signal strength of the predetermined ratio to the peak value of the insertion object image signal is 20% of the peak value of the insertion object image signal, as shown in FIG. 8, the first signal width detector 11 detects a signal width W1 of an insertion object image signal SA having a signal strength of 0.2, which is 20% of 1.0 that is the peak value of the signal strength E of the insertion object image signal SA, as a first signal width W1. Here, the insertion object image signal SA shown in FIG. 8 is a signal standardized so that the peak value of the signal strength E is 1.0, and in the following description, similarly, it is assumed that the insertion object image signal SA is standardized so that the peak value is 1.0 in a case where the insertion object image signal SA is shown.

In step S6, the insertion object display image signal generator 12 determines whether or not the first signal width W1 detected in step S5 is larger than a predetermined second signal width W2. In a case where the first signal width W1 is larger than the second signal width W2, the insertion object display image signal generator 12 generates an insertion object display image signal having a maximum width corresponding to the second signal width W2 in step S7.

Here, as shown in FIG. 8, for example, the insertion object display image signal generator 12 sets a portion having a center at a peak position P0 at which the signal strength E is the peak value of 1.0 and ranging from the center to the predetermined second signal width W2, in the insertion object image SA, as an insertion object display image signal SB. Here, a thin line FL in FIG. 8 indicates an iso-strength line of the signal strength where the signal strength E is a constant value, for example, 0.8. It can be understood that the insertion object display image signal SB shown in FIG. 8 has small attenuation of the signal strength E and a large signal strength E in a wide range centering around the peak position P0.

In a case where the insertion object display image signal SB is generated in step S7, in step S8, the image superposing unit 7 superimposes the tomographic image of the subject and the image of the distal end portion FE of the insertion object 13 on the basis of the insertion object display image signal SB and the tomographic image signal generated in step S1 to be displayed on the display 9. In a case where the tomographic image of the subject and the image of the distal end portion FE of the insertion object 13 are superimposed and displayed on the display 9, the operation of the ultrasonic wave device 1 according to the first embodiment ends.

Further, in a case where it is determined in step S6 that the first signal width W1 is smaller than the predetermined second signal width W2, the insertion object display image signal generator 12 proceeds to step S9, and generates an insertion object display image signal having a maximum width smaller than the second signal width W2.

Figure 9:
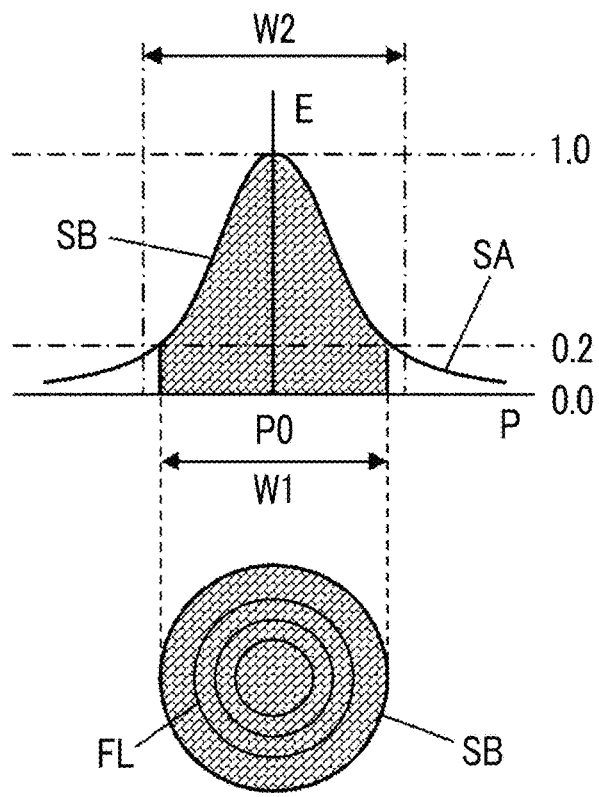
FIG. 9 is a conceptual diagram showing an insertion object display image signal in a case where the first signal width of the insertion object image signal is smaller than the second signal width in the first embodiment of the present invention.

Here, as shown in FIG. 9, for example, the insertion object display image signal generator 12 sets a portion having a center at a peak position P0 at which the signal strength E is the peak value of 1.0 and ranging from the center to the first signal width W1 smaller than the second signal width W2, in the insertion object image SA, as an insertion object display image signal SB. Here, three thin lines FL in FIG. 9 indicate iso-strength lines of the signal strengths E where the signal strengths E are 0.8, 0.6, and 0.4, respectively. It can be understood that the signal strength E of the insertion object display image signal SB shown in FIG. 9 is rapidly attenuated as the distance from the peak position P0 increases.

As shown in FIG. 9, in a case where the first signal width W1 is smaller than the predetermined second signal width W2, the first signal width W1 becomes the maximum width of the insertion object display image signal SB. Accordingly, in order to clearly display the image of the distal end portion FE of the insertion object 13 on the display 9, it is desirable that the first signal width W1 is a signal width of a portion having a signal strength larger than background noise of the insertion object image generating reception signal, in the insertion object image signal SA. That is, it is desirable that the predetermined ratio is set so that a signal strength of a predetermined ratio to the peak value of the signal strength E of the insertion object image signal SA is a signal strength higher than the background noise of the insertion object image generating reception signal.

In a case where the insertion object display image signal SB is generated in step S9, the tomographic image of the subject and the image of the distal end portion FE of the insertion object 13 are superimposed and displayed on the display 9 in step S8, and then, the operation of the ultrasonic wave device 1 according to the first embodiment ends.

Figure 10:
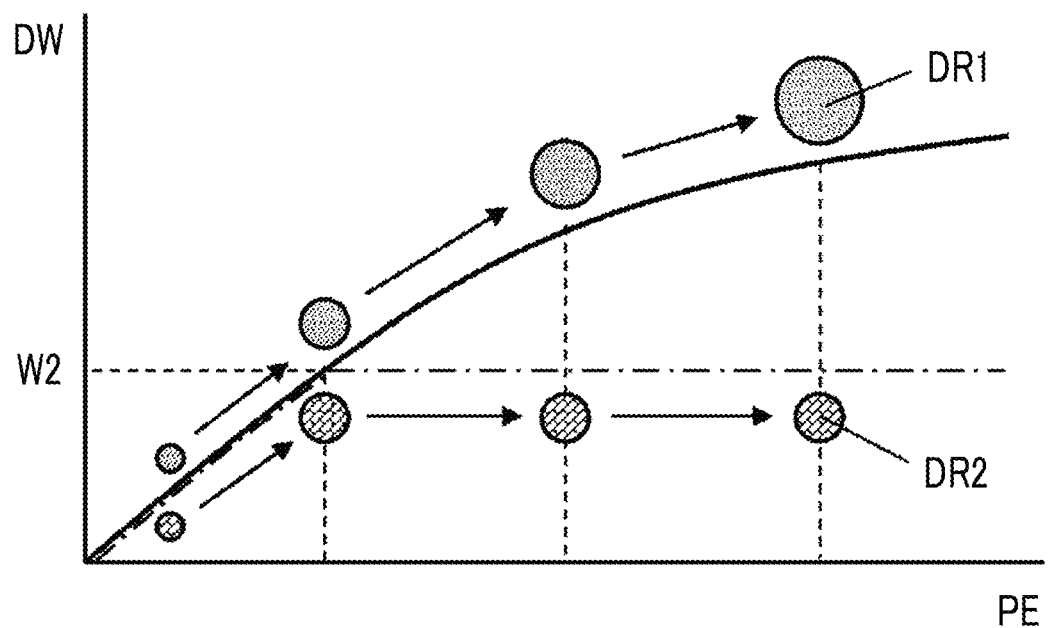
FIG. 10 is a diagram conceptually showing the size of an image of a distal end portion of an insertion object displayed in a related-art acoustic wave device and the size of the image of the distal end portion of the insertion object displayed in the first embodiment of the present invention.
Figure 11:
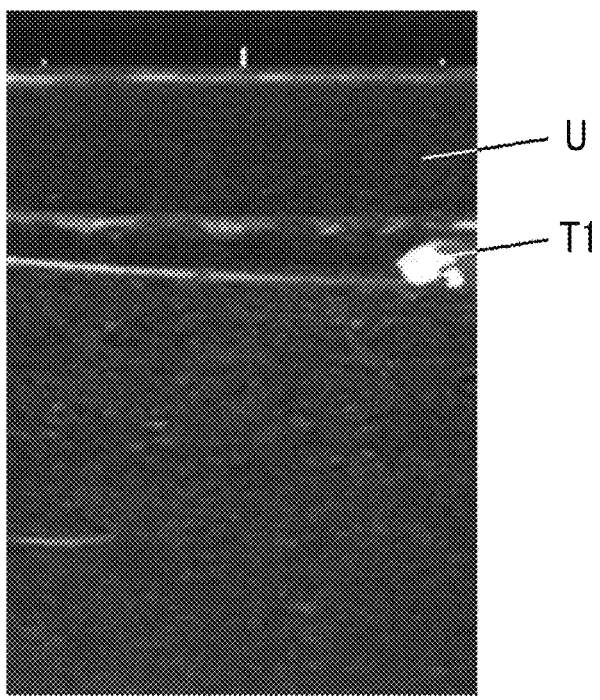
FIG. 11 is a diagram showing an example of the image of the distal end portion of the insertion object displayed in the related-art acoustic wave device.

Here, in an acoustic wave device such as a related-art ultrasonic wave device for generating a tomographic image of a subject, which includes an insertion object having a photoacoustic wave generator at a distal end portion thereof, for example, in a case where the distal end portion of the insertion object is inserted into a blood vessel, as shown in a display region DR1 in FIG. 10, as a maximum signal strength PE of an insertion object image generating reception signal corresponding to a photoacoustic wave from the photoacoustic wave generator becomes large, the photoacoustic wave in the vicinity of the distal end portion of the insertion object is not easily attenuated. Thus, a display width DW of the display region DR1 corresponding to the distal end portion of the insertion object becomes large. Accordingly, in the related-art acoustic wave device, for example, as shown in FIG. 11, an image T1 of the distal end portion of the insertion object in which an artifact has occurred is superimposed on a tomographic image U of the subject to be displayed on the display. This makes it difficult for a user to visually recognize a tissue or the like of the subject included in the tomographic image U, and thus, it is difficult for the user to confirm an accurate position of the distal end portion of the insertion object.

Figure 12:
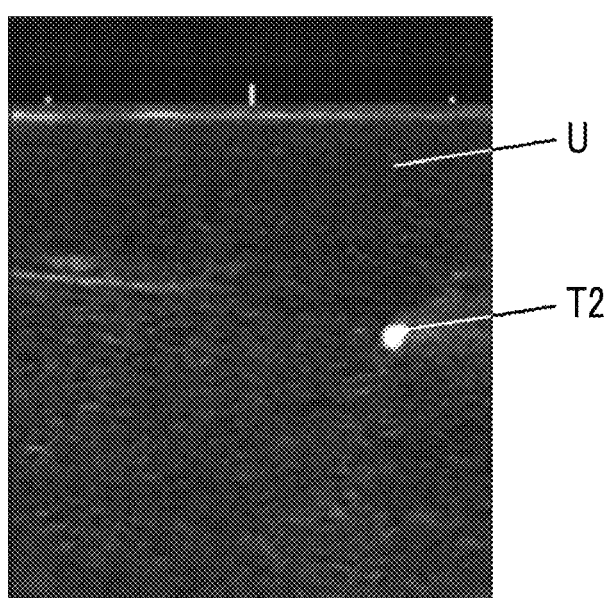
FIG. 12 is a diagram showing an example of the image of the distal end portion of the insertion object displayed in the ultrasonic wave device according to the first embodiment of the present invention.

On the other hand, according to the ultrasonic wave device 1 according to the first embodiment of the present invention, in a case where the first signal width W1 is larger than the predetermined second signal width W2, the insertion object display image signal SB having a maximum width corresponding to the second signal width W2 is generated, and in a case where the first signal width W1 is smaller than the second signal width W2, the insertion object display image signal SB having a maximum width smaller than the second signal width W2 is generated. Thus, as shown in a display region DR2 in FIG. 10, even in a case where the maximum signal strength PE of the insertion object image generating reception signal corresponding to the photoacoustic wave from the photoacoustic wave generator 21 becomes large, the display width DW corresponding to the display region DR2 of the distal end portion FE of the insertion object 13 may be set to be equal to or less than the second signal width W2. Accordingly, according to the ultrasonic wave device 1, for example, as shown in FIG. 12, an image T2 of the distal end portion FE of the insertion object 13 in which the influence of an artifact is suppressed is superimposed on the tomographic image U of the subject to be displayed on the display 9. Accordingly, it is possible to prevent a situation where the tissue of the subject included in the tomographic image U is not easily visually recognized by a user, to thereby make it possible for the user to accurately confirm the position of the distal end portion FE of the insertion object 13.

In a case where the first signal width W1 is equal to the second signal width W2, the insertion object display image signal SB having a maximum width corresponding to the second signal width W2 may be generated.

In the first embodiment, the insertion object image signal SA is generated in steps S2 to S4 after the tomographic image signal is generated in step S1, but the tomographic image signal may be generated after the insertion object image signal SA is generated.

Further, in the first embodiment, the insertion object display image signal generator 12 adjusts the maximum width of the insertion object display image signal SB depending on whether or not the first signal width W1 of the insertion object image signal SA is larger than the predetermined second signal width W2, but in a case where the first signal width W1 is equal to the second signal width W2, the insertion object display image signal generator 12 may perform a process of setting a portion having a center at the peak position P0 of the insertion object image signal SA and ranging up to the second signal width W2 as the insertion object display image signal SB, or may perform a process of setting a portion ranging from the peak position P0 to the first signal width W1 as the insertion object display image signal SB.

Second Embodiment

In the first embodiment, in a case where the first signal width W1 of the insertion object image signal SA is smaller than the predetermined second signal width W2, the insertion object display image signal generator 12 generates the insertion object display image signal SB having a maximum width corresponding to the first signal width W1, but in order to prevent a situation where the image of the distal end portion FE of the insertion object 13 is not easily visually recognized, a method for setting a lower limit with respect to the maximum width of the insertion object display image signal SB may be used.

The ultrasonic wave device 1 that is the acoustic wave device according to the second embodiment has the same configuration as in the ultrasonic wave device 1 according to the first embodiment shown in FIG. 1, and thus, detailed description of the configuration of the ultrasonic wave device 1 according to the second embodiment will not be repeated.

Figure 13:
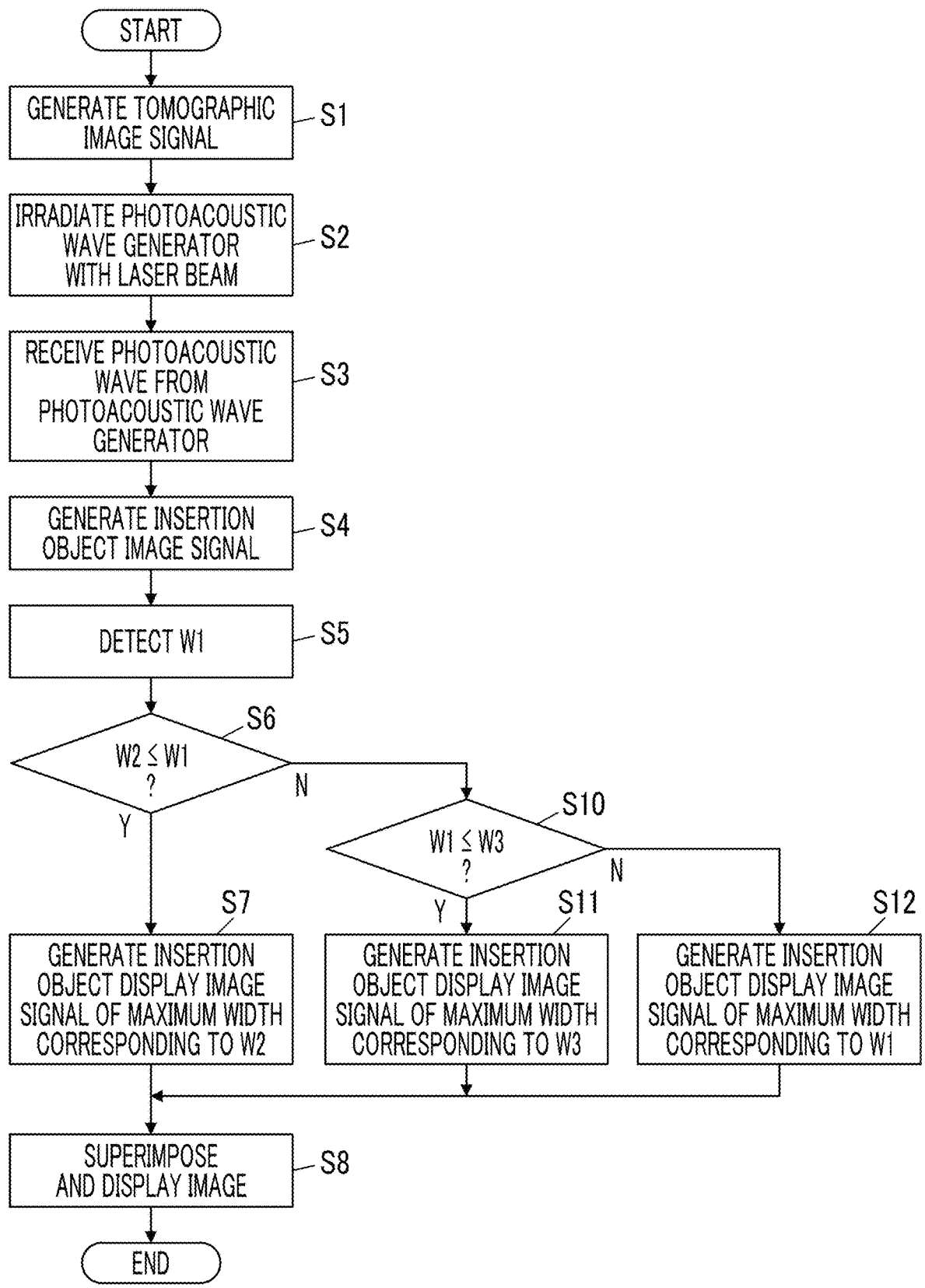
FIG. 13 is a flowchart showing an operation of an ultrasonic wave device according to a second embodiment of the present invention.

Hereinafter, an operation of the ultrasonic wave device 1 according to the second embodiment will be described with reference to the flowchart shown in FIG. 13. Steps S1 to S8 in a flowchart shown in FIG. 13 are the same as steps S1 to S8 in the first embodiment shown in FIG. 7. That is, a tomographic image of a subject is generated in step S1, and in step S2, in a case where laser beam is applied from the insertion object laser light source 14 to the photoacoustic wave generator 21 of the insertion object 13, the array transducer 2 receives a photoacoustic wave generated from the photoacoustic wave generator 21 in step S3 to generate an insertion object image generating reception signal, and generates an insertion object image signal SA from an insertion object image generating reception signal in step S4.

In a case where the first signal width W1 of the insertion object image signal SA is detected in the subsequent step S5, the insertion object display image signal generator 12 determines whether or not the first signal width W1 is larger than the predetermined second signal width W2. In a case where the first signal width W1 is larger than the second signal width W2, in step S7, the insertion object display image signal generator 12 sets a portion having a center at the peak position P0 of the insertion object image signal SA and having a maximum width corresponding to the second signal width W2 in the insertion object image signal SA as the insertion object display image signal SB. In the following step S8, the image superposing unit 7 superimposes the tomographic image of the subject and the image of the distal end portion FE of the insertion object 13 to be displayed on the display 9, on the basis of the tomographic image signal generated in step S1 and the insertion object display image signal SB generated in step S7.

In a case where it is determined in step S6 that the first signal width W1 of the insertion object image signal SA is smaller than the predetermined second signal width W2, in step S10, the insertion object display image signal generator 12 determines whether or not the first signal width W1 is smaller than a predetermined third signal width W3. Here, the third signal width W3 is a signal width smaller than the second signal width W2, which is set as a lower limit value of a maximum width with respect to the image of the distal end portion FE of the inserted object 13. The size of the third signal width W3 is not particularly limited as long as a user can easily visually recognize the image of the distal end portion FE of the insertion object 13. For example, the third signal width W3 may be set to the size of a minimum pixel of the display 9 and the size of a wavelength of an acoustic wave that propagates in the subject, and more specifically, may be set to 0.3 mm, for example.

In a case where the first signal width W1 is smaller than the third signal width W3, the insertion object display image signal generator 12 generates an insertion object display image signal SB having a maximum width corresponding to the third signal width W3 in step S11.

Figure 14:
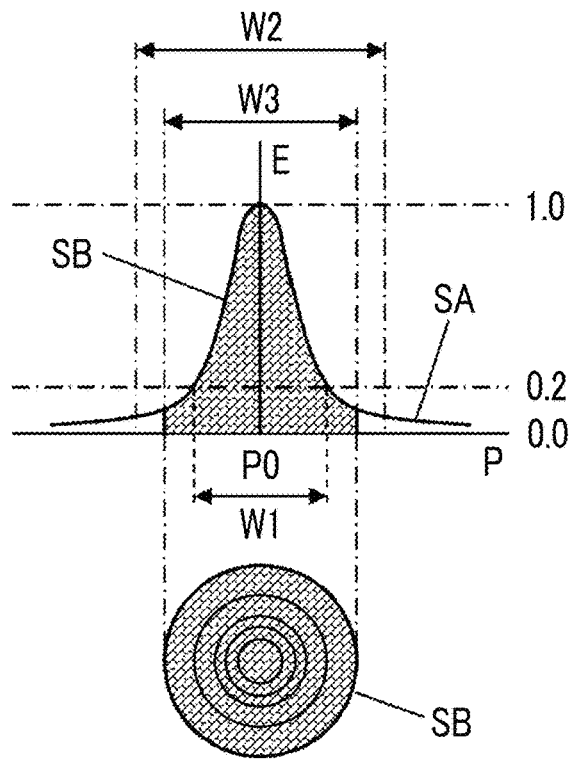
FIG. 14 is a conceptual diagram showing an insertion object display image signal in a case where a first signal width of an insertion object image signal is smaller than a third signal width in the second embodiment of the present invention.

Here, as shown in FIG. 14, for example, the insertion object display image signal generator 12 sets a portion having a center at the peak position P0 at which the signal strength E is the peak value of 1.0 and ranging from the center to the third signal width W3, in the insertion object image SA, as the insertion object display image signal SB.

In a case where the insertion object display image signal SB is generated in step S11, in step S8, the image superposing unit 7 superimposes the tomographic image of the subject and the image of the distal end portion FE of the insertion object 13, on the basis of the tomographic image signal of the subject generated in step S1 and the insertion object display image signal SB generated in step S11, to be displayed on the display 9.

Further, in a case where it is determined in step S10 that the first signal width W1 is larger than the third signal width W3, the insertion object display image signal generator 12 generates the insertion object display image signal SB having a maximum width corresponding to the first signal width W1 in step S12.

Figure 15:
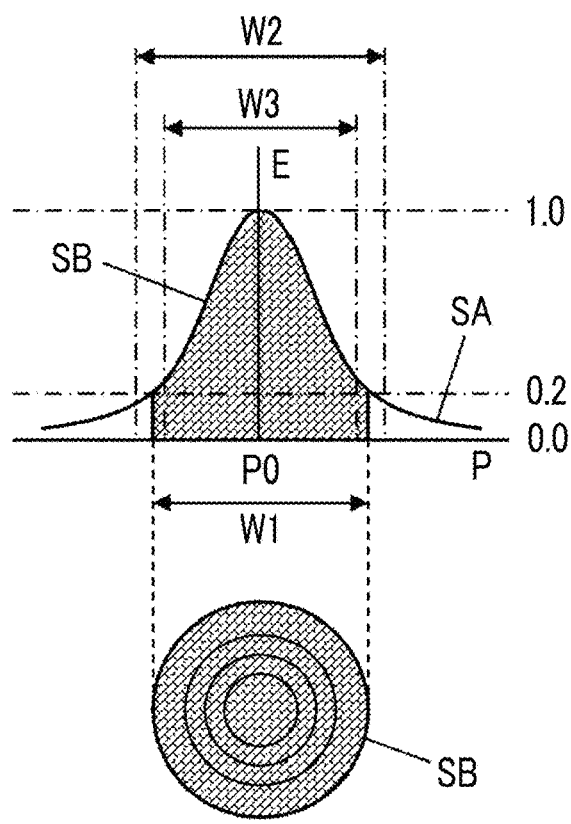
FIG. 15 is a conceptual diagram showing an insertion object display image signal in a case where the first signal width of the insertion object image signal is smaller than a second signal width and larger than the third signal width in the second embodiment of the present invention.

Here, as shown in FIG. 15, for example, the insertion object display image signal generator 12 sets a portion having a center at the peak position P0 and ranging from the center to the first signal width W1, in the insertion object image signal SA, as the insertion object display image signal SB.

In a case where the insertion object display image signal SB is generated in step S12, the tomographic image of the subject and the image of the distal end portion FE of the insertion object 13 are superimposed and displayed on the display 9 in step S8, and the operation of the ultrasonic wave device 1 according to the second embodiment ends.

In a case where the first signal width W1 of the insertion object image signal SA is equal to the second signal width W2 in step S6, the procedure may proceed to step S7 to set a portion having a maximum width corresponding to the second signal width W2 in the insertion object image signal SA as the insertion object display image signal SB, or the procedure may proceed to step S10 to determine whether or not the first signal width W1 is smaller than the third signal width W3. However, in a case where the procedure proceeds to step S10, since the first signal width W1 is equal to the second signal width W2 and is larger than the third signal width W3, the procedure further proceeds to step S12 to generate the insertion object display image signal SB having a maximum width corresponding to the first signal width W1.

In a case where the first signal width W1 is equal to the third signal width W3 in step S10, the procedure may proceed to step S11 to generate the insertion object display image signal SB having a maximum width corresponding to the third signal width W3, or the procedure may proceed to step S12 to generate the insertion object display image signal SB having a maximum width corresponding to the first signal width W1.

As described above, according to the ultrasonic wave device 1 according to the second embodiment, in a case where the first signal width W1 of the insertion object image signal SA is smaller than the third signal width W3 that is smaller than the predetermined second signal width W2, since the maximum width of the insertion object display image signal SB can be set to be equal to or larger than the third signal width, the width of the image of the distal end portion FE of the insertion object 13 can be displayed small, and thus, it is possible to prevent a situation where the image of the distal end portion FE of the insertion object 13 is not easily visually recognized by a user.

In the second embodiment, in a case where the first signal width W1 of the insertion object image signal SA is smaller than the predetermined second signal width W2, the maximum width of the insertion object display image signal SB is adjusted depending on whether or not the first signal width W1 is smaller than the third signal width W3, but in a case where the first signal width W1 is equal to the third signal width W3, the insertion object display image signal generator 12 may perform a process of generating an insertion object display image signal SB on the basis of a portion having a center at the peak position P0 of the insertion object image signal SA and ranging from the peak position P0 to the third signal width W3, or may perform a process of setting a portion ranging from the peak position P0 to the first signal width W1 as the insertion object display image signal SB.

Third Embodiment

In the second embodiment, in a case where the first signal width W1 of the insertion object image signal SA is smaller than the third signal width W3, the insertion object display image signal SB of which the maximum width is the third signal width W3 is generated, but at this time, the insertion object display image signal SB may be generated on the basis of the image signal obtained by enlarging the insertion object image signal SA, and thus, it is possible to obtain a state where the image of the distal end portion FE of the insertion object 13 is easily visually recognized by a user.

Figure 16:
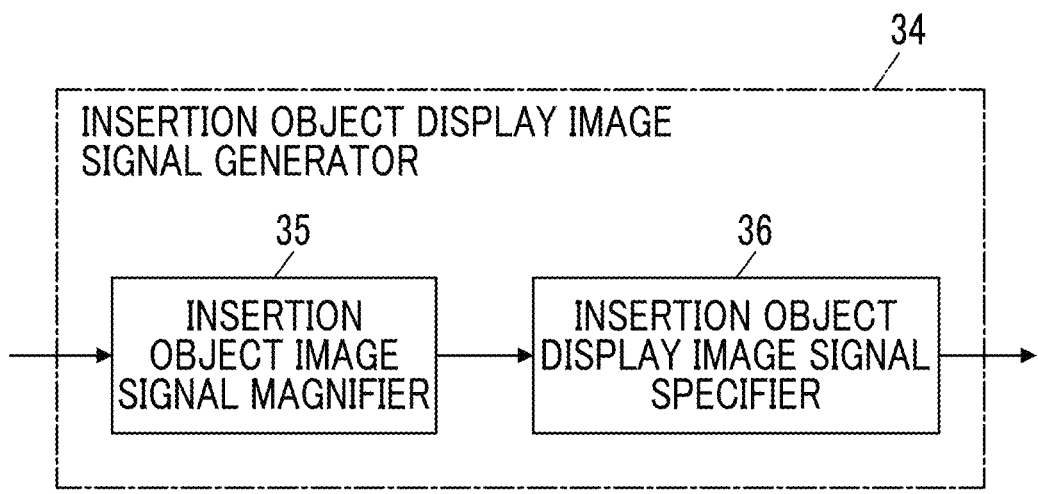
FIG. 16 is a block diagram showing an internal configuration of an insertion object display image signal generator according to a third embodiment of the present invention.

An ultrasonic wave device that is an acoustic wave device according to a third embodiment has the same configuration as in the ultrasonic wave device in the first embodiment shown in FIG. 1, except that the insertion object display image signal generator 34 shown in FIG. 16 is used instead of the insertion object display image signal generator 12. The insertion object display image signal generator 34 according to the third embodiment has a configuration in which an insertion object image signal magnifier 35 and an insertion object display image signal specifier 36 are connected in series.

Figure 17:
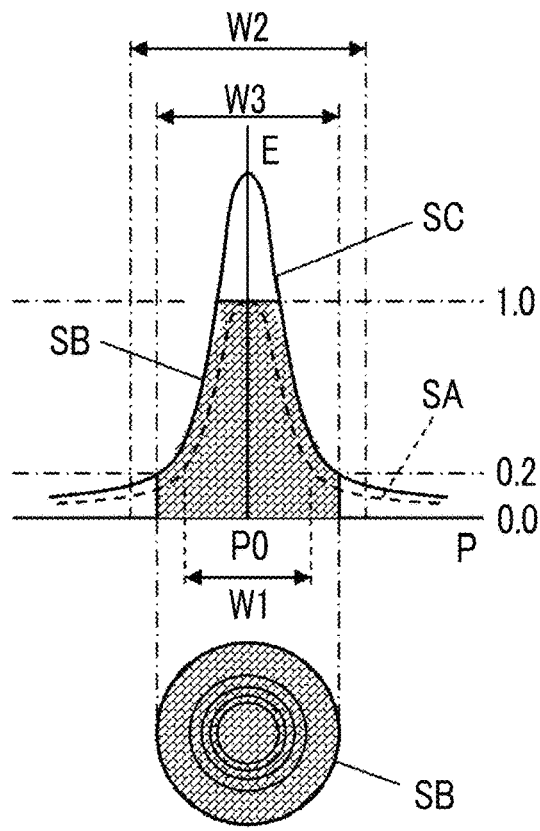
FIG. 17 is a conceptual diagram showing an enlarged image signal and an insertion object display image signal according to the third embodiment of the present invention.

The insertion object image signal magnifier 35 of the insertion object display image signal generator 34 generates an enlarged image signal obtained by enlarging the insertion object image signal SA until a signal width having a signal strength of a predetermined ratio to the peak value of the signal strength E of the insertion object image signal SA generated by the insertion object image signal generator 10 becomes larger than the third signal width W3. For example, the insertion object image signal magnifier 35 may increase a signal strength of at least a portion having a center as the peak position P0 of the insertion object image signal SA and ranging from the center to the third signal width W3, in the insertion object image signals SA, at a predetermined magnification. As a specific example, for example, in a case where the signal strength of the predetermined ratio to the peak value of the signal strength E of the insertion object image signal SA is 20% of the peak value of the signal strength E of the insertion object image signal SA, as shown in FIG. 17, the insertion object image signal magnifier 35 may increase the overall signal strength E of the insertion object image signal SA at a predetermined magnification until the signal width having the signal strength of 20% of the peak value of the signal strength E of the insertion object image signal SA becomes the third signal width W3, to thereby generate an enlarged image signal SC.

The insertion object display image signal specifier 36 of the insertion object display image signal generator 34 specifies a portion to be used as the insertion object display image signal SB in the enlarged image signal SC generated by the insertion object image signal magnifier 35. The insertion object display image signal specifier 36 performs the same process as the process performed by the insertion object display image signal generator 12 in the first and second embodiments with respect to the enlarged image signal SC. For example, as shown in FIG. 17, the insertion object display image signal specifier 36 sets a portion having a center at the peak position P0 of the enlarged image signal SC and ranging from the center to the third signal width W3, in the enlarged image signal SC, as the insertion object display image signal SB.

By increasing the overall signal strength E of the insertion object image signal SA at the predetermined magnification, a portion where the signal strength E in the enlarged image signal SC exceeds 1.0 is saturated, and in the insertion object display image signal SB, the signal strength E is represented as 1.0.

As described above, according to the ultrasonic wave device according to the third embodiment, in a case where the first signal width W1 of the insertion object image signal SA is smaller than the third signal width W3, since the enlarged image signal SC obtained by enlarging the insertion object image signal SA is generated and the insertion object display image signal SB is generated from the enlarged image signal SC, it is possible to obtain a state where the image of the distal end portion FE of the insertion object 13 is easily visually recognized by a user.

As shown in FIG. 17, as an example of the enlarged image signal SC generated by the insertion object image signal magnifier 35, the enlarged image signal SC is generated by increasing the signal strength E of the insertion object image signal SA at a predetermined magnification is shown. However, as long as the insertion object image signal SA can be enlarged until the signal width having the signal strength of the predetermined ratio to the peak value of the insertion object image signal SA becomes larger than the third signal width W3, the enlarged image signal SC is not limited thereto.

Figure 18:
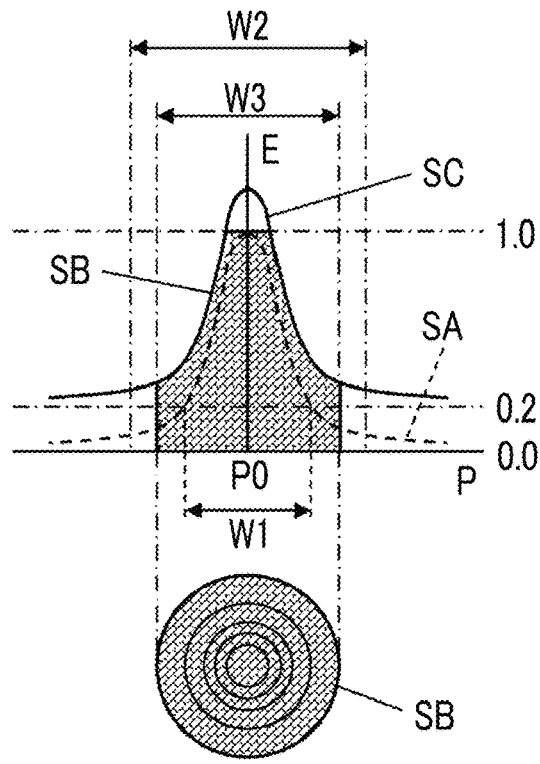
FIG. 18 is a conceptual diagram showing an enlarged image signal and an insertion object display image signal according to a modification example of the third embodiment of the present invention.

For example, the insertion object image signal magnifier 35 may increase a signal strength of at least a portion having a center at the peak position P0 of the insertion object image signal SA and ranging from the center to the third signal width W3 by a predetermined offset amount, to thereby generate the enlarged image signal SC. As a specific example, for example, as shown in FIG. 18, the insertion object image signal magnifier 35 may increase the overall insertion object image signal SA by a predetermined offset amount of 0.2, to thereby generate the enlarged image signal SC.

In this case, similarly, as the overall insertion object image signal SA increases by the predetermined offset amount, a portion where the signal strength E exceeds 1.0 in the enlarged image signal SC is saturated, and in the insertion object display image signal SB, the signal strength E is displayed as 1.0.

Figure 19:
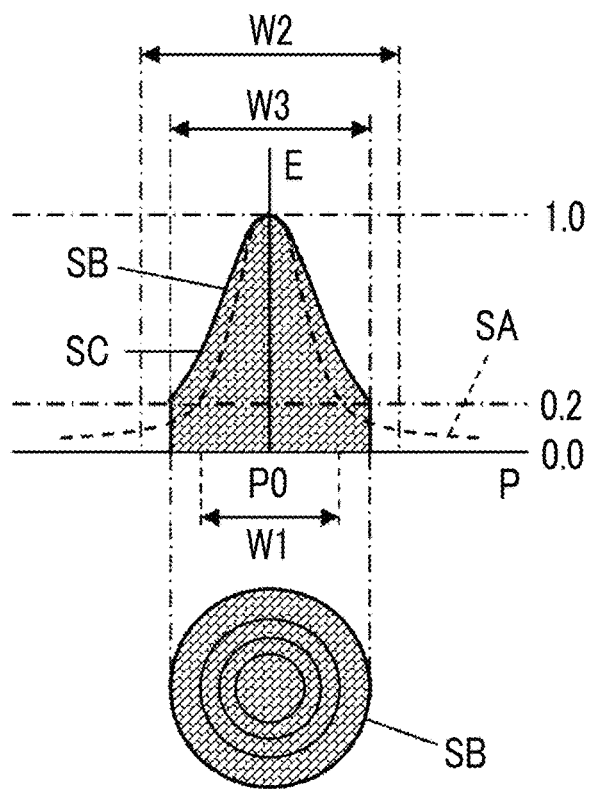
FIG. 19 is a conceptual diagram showing an enlarged image signal and an insertion object display image signal according to another modification example of the third embodiment of the present invention.

In addition, for example, the insertion object image signal magnifier 35 may enlarge a signal width of at least a portion having a signal strength larger than the signal strength of the predetermined ratio to the peak value of the signal strength E of the insertion object image signal SA in the insertion object image signal SA at a predetermined magnification, to thereby generate the enlarged image signal SC. As a specific example, for example, as shown in FIG. 19, in a case where the signal strength of the predetermined ratio to the peak value of the signal strength E of the insertion object image signal SA is a signal strength of 20% of the peak value of the signal strength E of the insertion object image signal SA, the insertion object image signal magnifier 35 may enlarge a signal width of a portion having the signal strength of 20% to 100% of the peak value of the signal strength E of the insertion object image signal SA at a predetermined magnification so that the signal width of the portion having the signal strength of 20% of the peak value of the signal strength E of the insertion object image signal SA becomes equal to the third signal width W3, to thereby generate the enlarged image signal SC.

Figure 20:
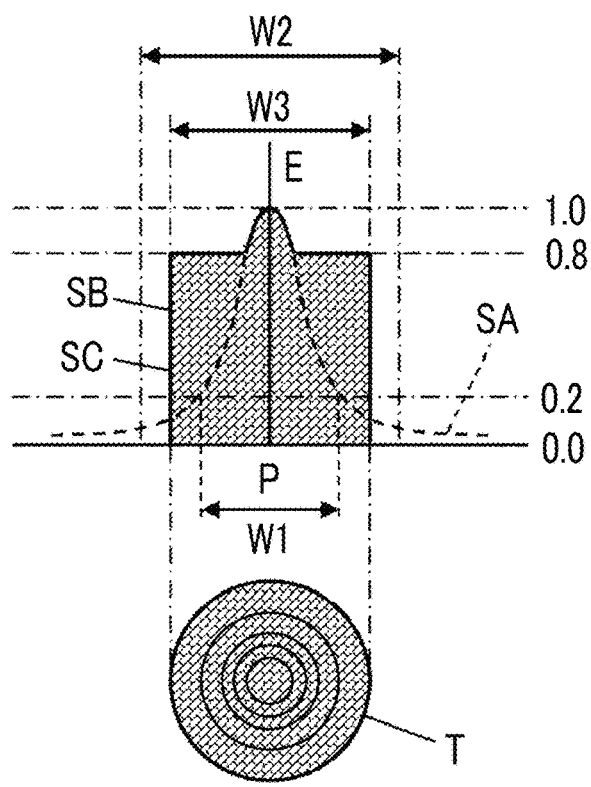
FIG. 20 is a conceptual diagram showing an enlarged image signal and an insertion object display image signal according to still another modification example of the third embodiment of the present invention.

In addition, for example, the insertion object image signal magnifier 35 may uniformly increase a signal strength of a portion where the signal strength is smaller than a predetermined signal strength, in at least the portion having the center at the peak position P0 and ranging from the center to the third signal width W3, in the insertion object image signal SA until the signal strength becomes the predetermined signal strength, to thereby generate the enlarged image signal SC. As a specific example, for example, as shown in FIG. 20, in a case where the predetermined signal strength is 0.8, the insertion object image signal magnifier 35 may uniformly increase a signal strength of a portion where the signal strength is smaller than 0.8, in the portion having the center at the peak position P0 and ranging up to the third signal width W3, up to 0.8, to thereby generate the enlarged image signal SC.

Figure 21:
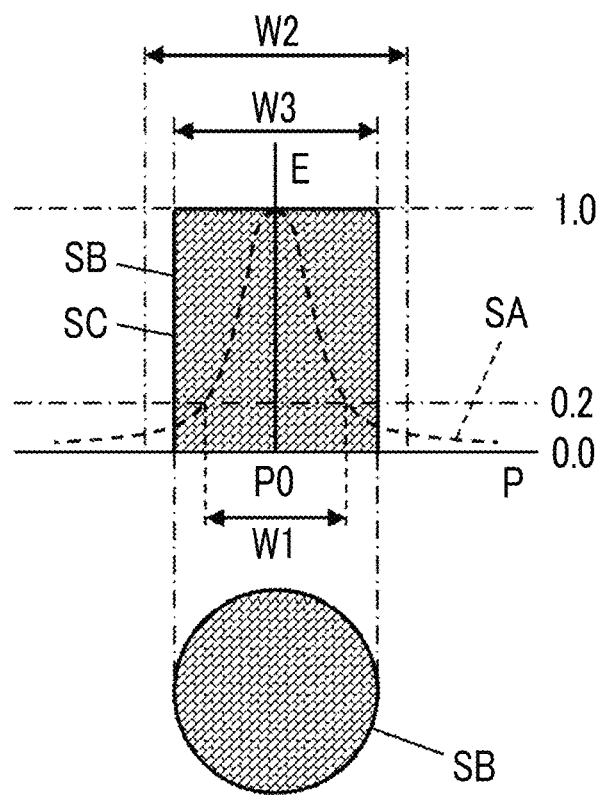
FIG. 21 is a conceptual diagram showing an enlarged image signal and an insertion object display image signal according to still another modification example of the third embodiment of the present invention.

Further, for example, the insertion object image signal magnifier 35 may increase the signal strength of at least the portion having the center at the peak position P0 and ranging from the center to the third signal width W3 in the insertion object image signal SA up to the peak value of the insertion object image signal SA, to thereby generate the enlarged image signal SC. As a specific example, for example, as shown in FIG. 21, the insertion object image signal magnifier 35 may increase the signal strength up to the peak value of 1.0, in the portion having the center at the peak position P0 and ranging up to the third signal width W3, to thereby generate the enlarged image signal SC.

Fourth Embodiment

According to the first to third embodiments, since the insertion object display image signal SB of which the maximum width is adjusted according to the size of the first signal width W1 of the insertion object image signal SA is generated, as a result, the maximum width of the insertion object display image signal SB may be enlarged or reduced with respect to the first signal width W1 of the insertion object image signal SA. Accordingly, it is possible to cause a user to recognize whether the maximum width of the insertion object display image signal SB corresponding to the image of the distal end portion FE of the insertion object 13 is enlarged or reduced from the first signal width W1 of the insertion object image signal SA, and thus, it is possible to urge the user to pay attention to a positional relationship of the distal end portion FE of the insertion object 13 in the subject.

Figure 22:
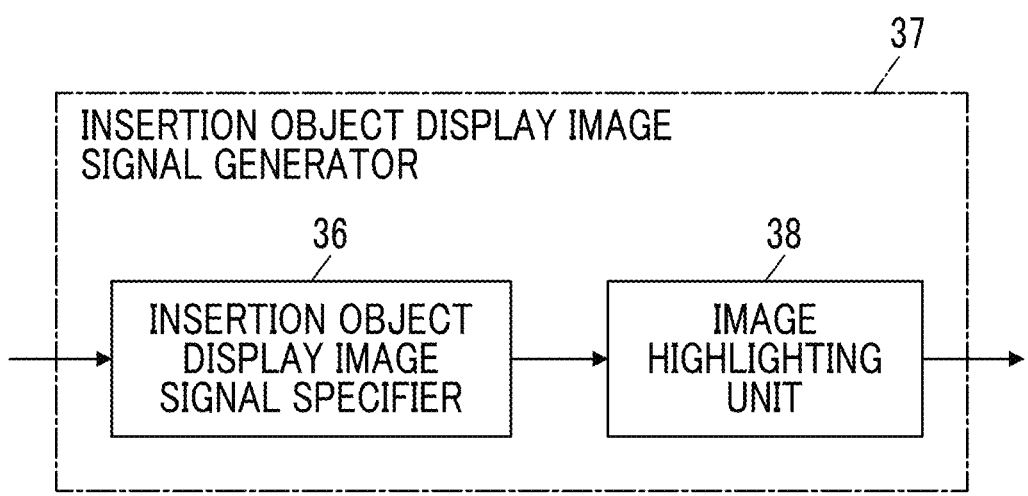
FIG. 22 is a diagram showing an internal configuration of an insertion object display image signal generator according to a fourth embodiment of the present invention.

An ultrasonic wave device that is an acoustic wave device according to the fourth embodiment has the same configuration as in the ultrasonic wave device 1 of the first embodiment shown in FIG. 1, except that the insertion object display image signal generator 37 shown in FIG. 22 is used instead of the insertion object display image signal generator 12. The insertion object display image signal generator 37 according to the fourth embodiment has a configuration in which an insertion object display image signal specifier 36 and an image highlighting unit 38 are connected in series. Here, the insertion object display image signal specifier 36 according to the fourth embodiment is the same as the insertion object display image signal specifier 36 according to the third embodiment, and specifies a portion of the insertion object image signal SA generated by the insertion object image signal generator 10 to be used as the insertion object display image signal SB.

In a case where the maximum width of the insertion object display image signal SB is different from the first signal width W1 of the insertion object image signal SA, that is, in a case where the maximum of the insertion object display image signal SB is an enlarged or reduced from the first signal width W1 of the insertion object image signal SA, the image highlighting unit 38 of the insertion object display image signal generator 37 highlights and displays the image of the distal end portion FE of the insertion object 13 on the display 9.

Figure 23:
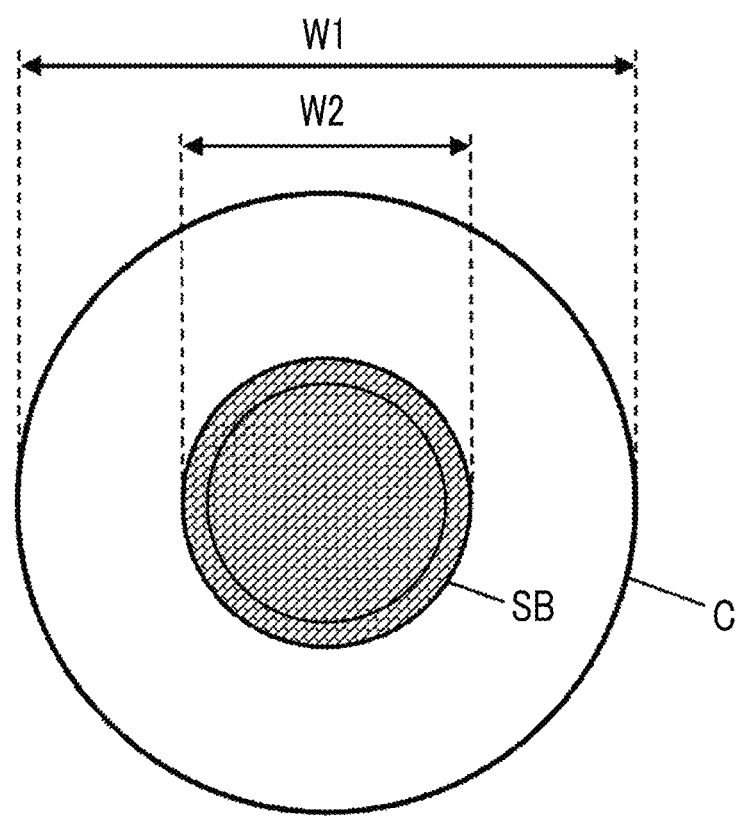
FIG. 23 is a diagram schematically showing an outline of a region having a first signal width larger than a second signal width according to the fourth embodiment of the present invention.

For example, the image highlighting unit 38 may superimpose an outline of a region having a center at the peak position P0 of the insertion object image signal SA and having the first signal width W1 on the image of the distal end portion FE of the insertion object 13 of the insertion object image signal SA to be displayed on the display 9. For example, in a case where the first signal width W1 of the insertion object image signal SA is larger than the predetermined second signal width W2, as shown in FIG. 23, the image highlighting unit 38 generates an outline image signal C having a center at the peak position P0 and corresponding to an outline of a region having the first signal width W1 surrounding the insertion object display image signal SB, and adds the outline image signal C to the insertion object display image signal SB. By recognizing an image of an outline positioned to surround the image of the distal end portion FE of the insertion object 13, it is possible for a user to understand that the maximum width of the insertion object display image signal SB is reduced from the first signal width W1 of the insertion object image signal SA.

Figure 24:
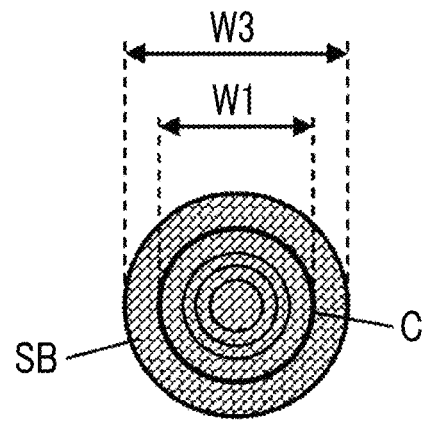
FIG. 24 is a diagram schematically showing an outline of a region having the first signal width smaller than a third signal width according to the fourth embodiment of the present invention.

Further, for example, in a case where the first signal width W1 of the insertion object image signal SA is smaller than the predetermined third signal width W3, as shown in FIG. 24, the image highlighting unit 38 generates an outline image signal C having a center at the peak position P0 and corresponding to the outline of the region of the first signal width W1 included in the insertion object display image signal SB, and adds the outline image signal C to the insertion object display image signal SB. By recognizing an image of an outline positioned to surround the image of the distal end portion FE of the insertion object 13, it is possible for a user to understand that the maximum width of the insertion object display image signal SB is enlarged from the first signal width W1 of the insertion object image signal SA.

As described above, according to the ultrasonic wave device according to the third embodiment, depending on whether the maximum width of the insertion object display image signal SB is enlarged or reduced from the first signal width W1 of the insertion object image signal SA, in order to highlight and display the image of the distal end portion FE of the insertion object 13, it is possible to make a user recognize whether the maximum width of the image of the distal end portion FE of the insertion object 13 is enlarged or reduced from the first signal width W1 of the insertion object image signal SA, and to urge the user to pay attention to a positional relationship of the distal end portion FE of the insertion object 13 in the subject.

By adding the outline image signal C that represents the outline to the insertion object display image signal SB, the image highlighting unit 38 of the insertion object display image signal generator 37 highlights and displays the image of the distal end portion FE of the insertion object 13, but between a case where the maximum width of the insertion object display image signal SB is reduced from the first signal width W1 and a case where the maximum width is enlarged therefrom, the outlines corresponding to the outline image signals C may be displayed on the display 9 in different display modes. For example, between a case where the maximum width of the insertion object display image signal SB is reduced from the first signal width W1 and a case where the maximum width is enlarged therefrom, the image highlighting unit 38 may display the outlines corresponding to the outline image signals C in different colors. In addition, for example, between a case where the maximum width of the insertion object display image signal SB is reduced from the first signal width W1 and a case where the maximum width is enlarged therefrom, the image highlighting unit 38 may configure the outlines corresponding to the outline image signals C by different types of lines such as a solid line and a broken line. Thus, it is possible for a user to clearly recognize whether the maximum width of the image of the distal end portion FE of the insertion object 13 is enlarged or reduced from the first signal width W1 of the insertion object image signal SA.

In addition, as long as a user can recognize whether the maximum width of the insertion object display image signal SB is enlarged or reduced from the first signal width W1 of the insertion object image signal SA, the highlighting display of the image of the distal end portion FE of the insertion object 13 is not limited to the addition of the outline image signal C to the insertion object display image signal SB.

Figure 25:
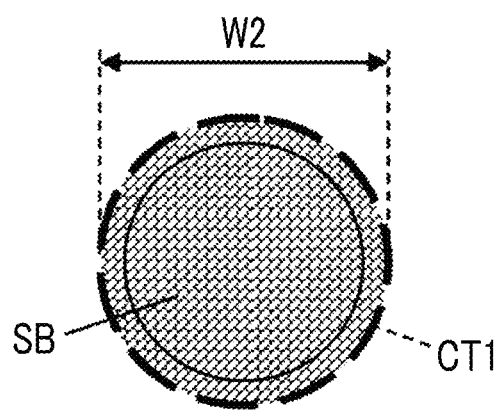
FIG. 25 is a diagram schematically showing an outer peripheral portion of an image of a distal end portion of an insertion object in a case where a first signal width is larger than a second signal width in a modification example of the fourth embodiment of the present invention.
Figure 26:
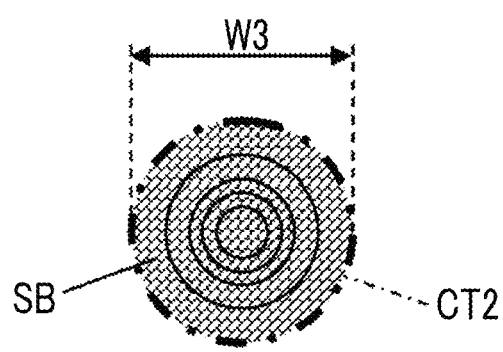
FIG. 26 is a diagram schematically showing an outer peripheral portion of an image of the distal end portion of the insertion object in a case where the first signal width is smaller than a third signal width in the modification example of the fourth embodiment of the present invention.

For example, as shown in FIGS. 25 and 26, between a case where the maximum width of the insertion object display image signal SB is reduced from the first signal width W1 of the insertion object image signal SA and a case where the maximum width is enlarged therefrom, the image highlighting unit 38 may set outer peripheral portions CT1 and CT2 of the insertion object display image signal SB in different colors. Here, FIG. 25 shows a case where the maximum width of the insertion object display image signal SB is reduced from the first signal width W1 of the insertion object image signal SA to the second signal width W2, and FIG. 26 shows a case where the maximum width of the insertion object display image signal SB is enlarged from the first signal width W1 of the insertion object image signal SA to the third signal width W3. In addition, between a case where the maximum width of the insertion object display image signal SB is reduced from the first signal width W1 of the insertion object image signal SA and a case where the maximum width is enlarged therefrom, the outer peripheral portions CT1 and CT2 of the insertion object display image signal SB may be configured by different types of lines such as a solid line and a broken line, instead of setting the colors of the outer peripheral portions CT1 and CT2 of the insertion object display image signal SB to be different from each other.

Figure 27:
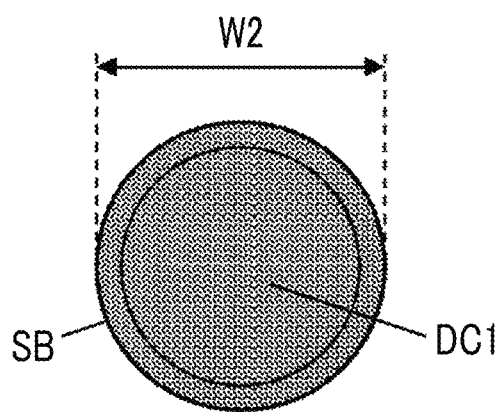
FIG. 27 is a diagram schematically showing an image of a distal end portion of an insertion object in a case where a first signal width is larger than a second signal width in another modification example of the fourth embodiment of the present invention.
Figure 28:
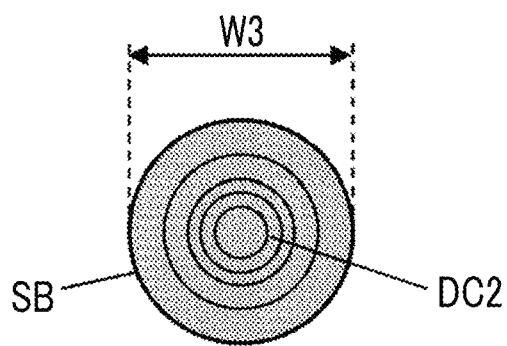
FIG. 28 is a diagram schematically showing an image of the distal end portion of the insertion object in a case where the first signal width is smaller than a third signal width in another modification example of the fourth embodiment of the present invention.

Further, for example, as shown in FIGS. 27 and 28, between a case where the maximum width of the insertion object display image signal SB is reduced from the first signal width W1 of the insertion object image signal SA and a case where the maximum width is enlarged therefrom, the image highlighting unit 38 may set the insertion object display image signal SB in different colors. Here, FIG. 27 shows a case where the maximum width of the insertion object display image signal SB is reduced from the first signal width W1 of the insertion object image signal SA to the second signal width W2, and shows that the insertion object display image signal SB has a first display color DC1. Further, FIG. 28 shows a case where the maximum width of the insertion object display image signal SB is enlarged from the first signal width W1 of the insertion object image signal SA to the third signal width W3, and shows that the insertion object display image signal SB has a second display color DC2.

Further, the insertion object display image signal generator 37 in the fourth embodiment may further include the insertion object image signal magnifier 35 according to the third embodiment. With this configuration, it is possible to use the third embodiment and the fourth embodiment of the present invention in combination.

Fifth Embodiment

In the first to fourth embodiments, in a case where the insertion object display image signal SB is generated, the first signal width W1 of the insertion object image signal SA is compared with the predetermined second signal width W2, but in this case, the second signal width W2 may be set by a user.

Figure 29:
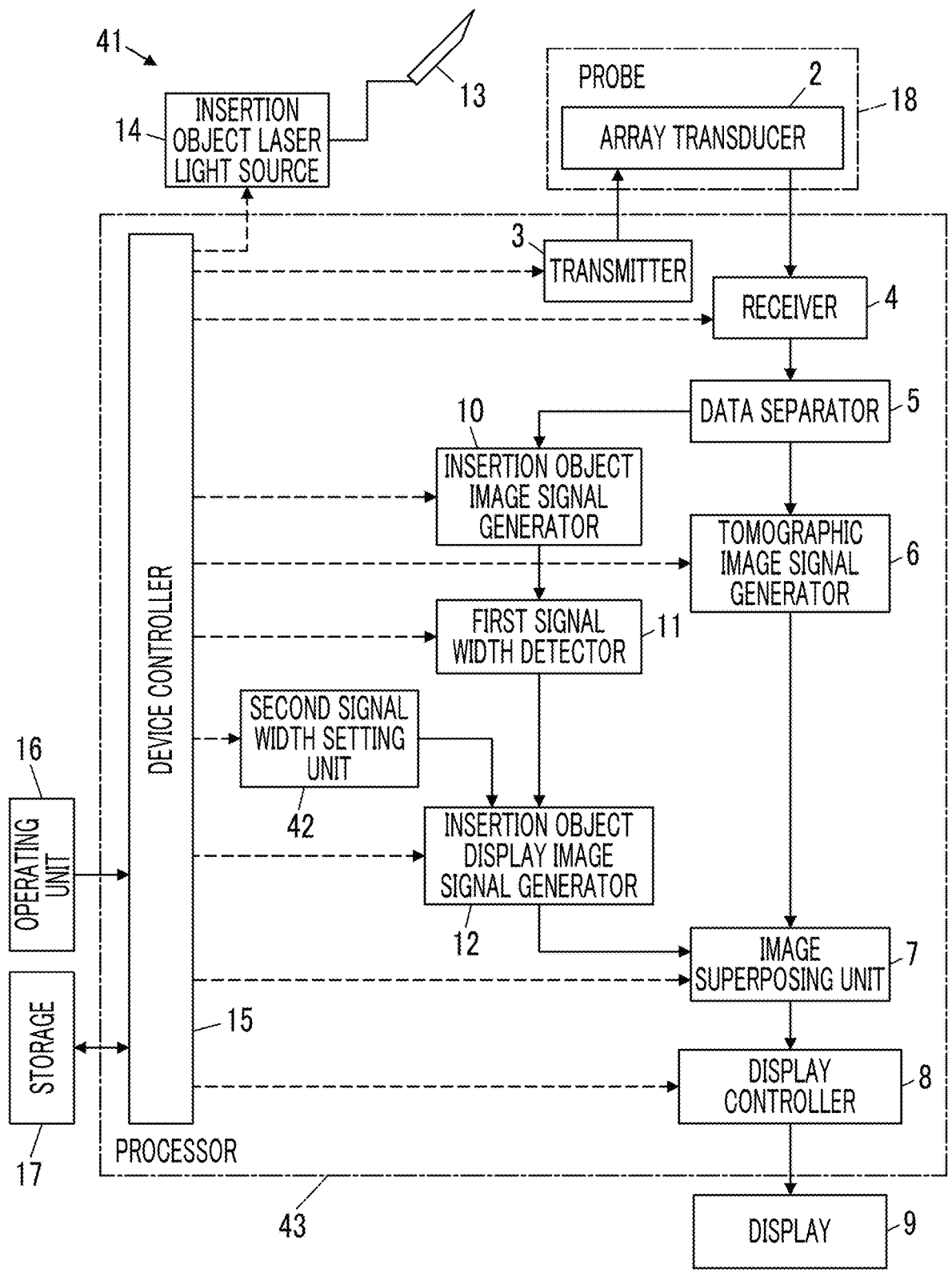
FIG. 29 is a block diagram showing a configuration of an ultrasonic wave device according to a fifth embodiment of the present invention.

FIG. 29 is a block diagram showing a configuration of an ultrasonic wave device 41 that is an acoustic wave device according to the fifth embodiment. The ultrasonic wave device 41 according to the fifth embodiment differs from the ultrasonic wave device 1 according to the first embodiment shown in FIG. 1 in that the ultrasonic wave device 41 further includes a second signal width setting unit 42 connected to the insertion object display image signal generator 12, in which the device controller 15 is connected to the second signal width setting unit 42. A processor 43 is configured by the transmitter 3, the receiver 4, the data separator 5, the tomographic image signal generator 6, the image superposing unit 7, the display controller 8, the insertion object image signal generator 10, the first signal width detector 11, the insertion object display image signal generator 12, the device controller 15, and the second signal width setting unit 42.

The second signal width setting unit 42 of the processor 43 sets the second signal width W2 to be compared with the first signal width W1 of the insertion object image signal SA in a case where the insertion object display image signal generator 12 generates the insertion object display image signal SB. For example, the second signal width setting unit 42 may set a value input by a user through the operating unit 16 as the second signal width W2.

Thus, according to the ultrasonic wave device 41 according to the fifth embodiment, since a user sets the second signal width W2 in advance, it is possible to adjust the size of the image of the distal end portion FE of the insertion object 13 so that a tissue or the like included in a tomographic image of a subject can be easily visually recognized.

Although not shown, for example, as the first signal width detector 11 is connected to the second signal width setting unit 42, the second signal width setting unit 42 may set the second signal width W2 on the basis of the first signal width W1 detected in a calibration medium such as water, ultrasonic jelly, or the like that is different from a subject. For example, more specifically, by applying laser beam from the insertion object laser light source 14 to the photoacoustic wave generator 21 of the insertion object 13 while the distal end portion FE of the insertion object 13 is positioned in the calibration medium to generate the insertion object image signal SA, the second signal width setting unit 42 may set a signal width having a signal strength having a predetermined ratio to the signal strength E of the insertion object image signal SA as the second signal width W2.

Figure 30:
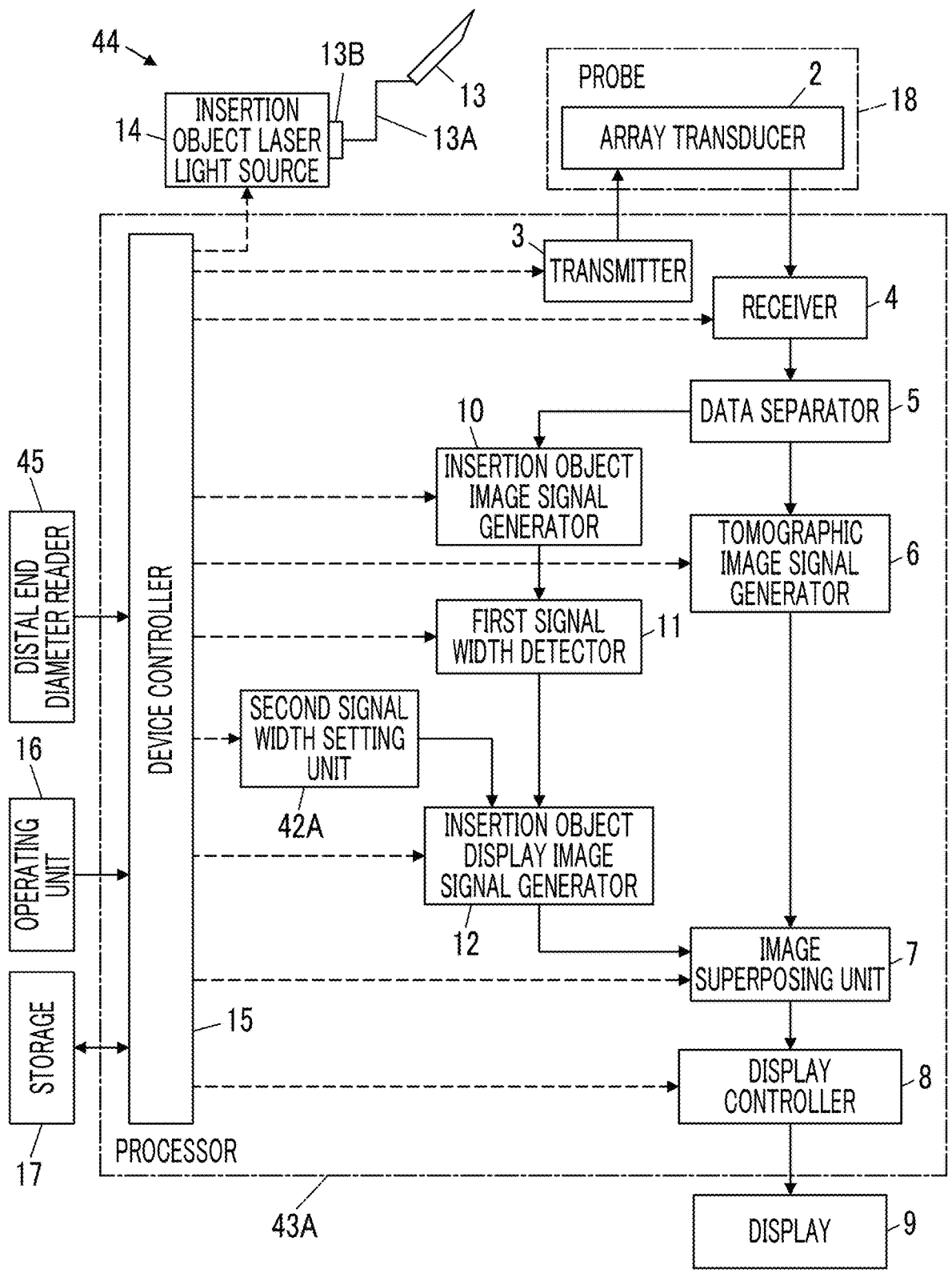
FIG. 30 is a block diagram showing a configuration of an ultrasonic wave device according to a modification example of the fifth embodiment of the present invention.

Further, in the fifth embodiment, the second signal width setting unit 42 sets a value set by a user as the second signal width W2, but may set the second signal width W2 by automatically reading information on the insertion object 13. FIG. 30 is a block diagram showing a configuration of an ultrasonic wave device 44 according to a modification example of the fifth embodiment. The ultrasonic wave device 44 includes a processor 43A having a second signal width setting unit 42A instead of the processor 43 having the second signal width setting unit 42, in the ultrasonic wave device 41 according to the fifth embodiment shown in FIG. 29, and further includes a distal end diameter reader 45 connected to the device controller 15.

For example, a distal end diameter recording unit configured by an integrated circuit (IC) tag, a bar code, or the like on which the diameter of the distal end portion FE of the insertion object 13 is recorded is attached at a root portion of the insertion object 13, a cable 13A connected to the insertion object 13, a connector 13B for connecting one end of the cable 13A to the insertion object laser light source 14, and the like, and the distal end diameter reader 45 automatically reads the diameter of the distal end portion FE of the insertion object 13 from the distal end diameter recording unit.

The second signal width setting unit 42A calculates a converted value by multiplying a value of the diameter read by the distal end diameter reader 45 by a predetermined coefficient, and sets the converted value as the second signal width W2.

Accordingly, according to the ultrasonic wave device 44 according to the modification example of the fifth embodiment, it is possible to accurately reflect an actual size of the distal end portion FE of the insertion object 13 to the image of the distal end portion FE of the insertion object 13 displayed on the display 9 in a state where a user does not need to input the value of the second signal width W2.

Sixth Embodiment

The first to fifth embodiments show examples in which the present invention is applied to the ultrasonic wave device that includes the insertion object 13 having the photoacoustic wave generator 21, but the present invention may be applied to a photoacoustic wave device that includes the insertion object 13 having the photoacoustic wave generator 21 and generates a tomographic image of a subject on the basis of photoacoustic waves emitted from a tissue or the like in a subject.

Figure 31:
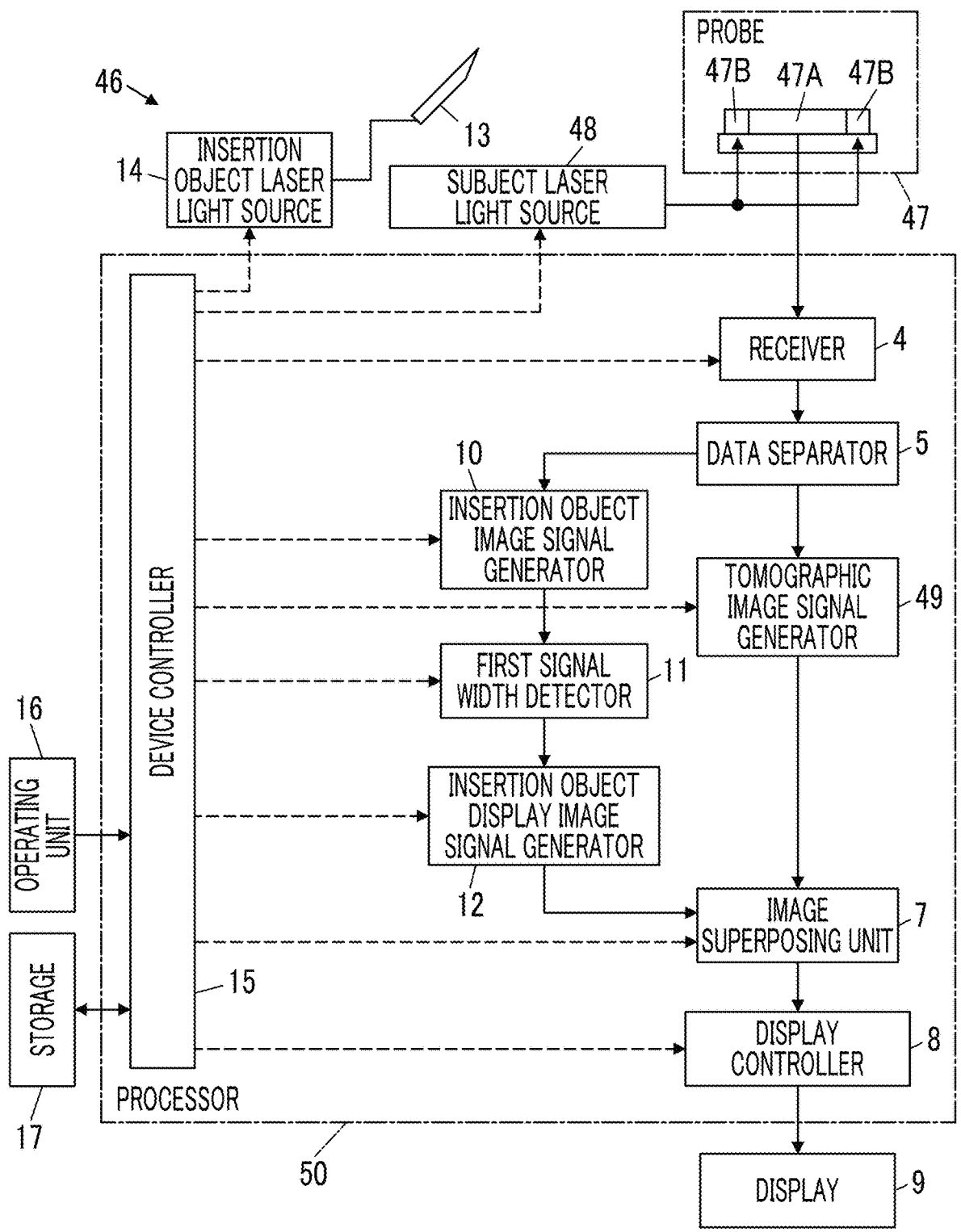
FIG. 31 is a block diagram showing a configuration of a photoacoustic wave device according to a sixth embodiment of the present invention.

FIG. 31 is a block diagram showing a configuration of a photoacoustic wave device 46 that is an acoustic wave device according to the sixth embodiment. The photoacoustic wave device 46 includes a probe 47 instead of the probe 18, includes a subject laser light source 48 connected to the probe 47 instead of the transmitter 3, and includes a processor 50 instead of the processor 19, in the ultrasonic wave device 1 according to the first embodiment shown in FIG. 1. The processor 50 includes a tomographic image signal generator 49 instead of the tomographic image signal generator 6 in the processor 19 of the first embodiment shown in FIG. 1. Except for these differences, the photoacoustic wave device 46 according to the sixth embodiment has the same configuration as in the ultrasonic wave device 1 according to the first embodiment. The probe 47 is configured to include an array transducer 47A and a subject laser beam irradiator 47B disposed adjacent to both ends of the array transducer 47A. The receiver 4 is connected to the array transducer 47A of the probe 47, and the subject laser light source 48 is connected to the two subject laser beam irradiators 47B of the probe 47. The device controller 15 is connected to the subject laser light source 48.

Further, the receiver 4, the data separator 5, the image superposing unit 7, the display controller 8, the insertion object image signal generator 10, the first signal width detector 11, the insertion object display image signal generator 12, the device controller 15, and the tomographic image signal generator 49 form the processor 50.

Although not shown, the subject laser beam irradiator 47B of the probe 47 and the subject laser light source 48 form a subject beam irradiator, and the array transducer 47A of the probe 47 and the receiver 4 form a reception signal generator.

The subject laser light source 48 shown in FIG. 31 has the same internal configuration as in the insertion object laser light source 14, and emits a pulsed laser beam under the control of the device controller 15.

The two subject laser beam irradiators 47B of the probe 47 are connected to the subject laser light source 48 by light guide members (not shown) such as optical fibers, respectively, and irradiate the inside of a subject with a pulsed laser beam from the subject laser light sources 48.

In a case where the pulsed laser beam is applied to a tissue of the subject from the subject laser beam irradiator 47B, in vivo substances such as glucose and hemoglobin included in the tissue of the subject absorb the pulsed laser beam to perform expansion and contraction, and emits an acoustic wave called a so-called photoacoustic wave.

The array transducer 47A of the probe 47 has the same configuration as in the array transducer 2 in the first embodiment shown in FIG. 1, generates a tomographic image generating reception signal on the basis of a photoacoustic wave emitted from the tissue of the subject, and generates an insertion object image generating reception signal on the basis of a photoacoustic wave emitted from the photoacoustic wave generator 21 of the insertion object 13.

The tomographic image generating reception signal generated by the array transducer 47A is output to the tomographic image signal generator 49 through the data separator 5. The tomographic image signal generator 49 has the same configuration as in the tomographic image signal generator 6 in the first embodiment shown in FIG. 1, and generates a tomographic image signal that represents a tomographic image of the subject from the tomographic image generating reception signal generated on the basis of the photoacoustic wave.

On the basis of the tomographic image signal and the insertion object display image signal SB generated by the insertion object display image signal generator 12, the image superposing unit 7 superimposes the tomographic image of the subject and the image of the distal end portion FE of the insertion object 13 to be displayed on the display 9.

As described above, according to the photoacoustic wave device 46 of the sixth embodiment, similarly to the ultrasonic wave device 1 of the first embodiment shown in FIG. 1, since the insertion object image signal generator 10, the first signal width detector 11, and the insertion object display image signal generator 12 are provided, as shown in FIG. 10, even though the maximum signal strength PE of the insertion object image generating reception signal corresponding to the photoacoustic wave from the photoacoustic wave generator 21 becomes large, the display width DW corresponding to the display region DR2 of the distal end portion FE of the insertion object 13 may be set to be equal to or less than the second signal width W2. Thus, according to the photoacoustic wave device 46, it is possible to prevent a situation where a tissue of a subject included in the tomographic image U is not easily visually recognized by a user, and it is possible for the user to accurately confirm the position of the distal end portion FE of the insertion object 13.

The various configurations described in the second to fifth embodiments may be also appropriately applied to the photoacoustic wave device 46 of the sixth embodiment.

From the above description, it is possible to provide an acoustic wave device described in the following appendix 1.

APPENDIX 1

An acoustic wave device comprising:
a probe;
a processor that irradiates inside a subject with an ultrasonic beam or laser beam from the probe;
an insertion object that can be inserted into the subject and has a photoacoustic wave generator at a distal end portion;
an insertion object laser light source that generates a photoacoustic wave from the photoacoustic wave generator by irradiating the photoacoustic wave generator of the insertion object with laser beam; and
a display,
wherein the processor
receives an acoustic wave emitted from a tissue of the subject to generate a tomographic image generating reception signal by irradiating the inside of the subject with the ultrasonic beam or the laser beam from the probe, and receives a photoacoustic wave by the photoacoustic wave generator to generate an insertion object image generating reception signal,
generates a tomographic image signal representing a tomographic image of the subject from the tomographic image generating reception signal,
generates an insertion object image signal representing an image of the distal end portion of the insertion object from the insertion object image generating reception signal,
detects a first signal width of the insertion object image signal having a signal strength of a predetermined ratio to a peak value of a signal strength in the insertion object image signal,
generates, in a case where the first signal width is larger than a predetermined second signal width, an insertion object display image signal having a center at a peak position where the signal strength of the insertion object image becomes the peak value and having a maximum width corresponding to the second signal width from the insertion object image signal, and generates, in a case where the first signal width is smaller than the second signal width, an insertion object display image signal having a center at the peak position and having a maximum width smaller than the second signal width from the insertion object image signal; and
superimposes the tomographic image of the subject and the image of the distal end portion of the insertion object to be displayed on the display on the basis of the tomographic image signal and the insertion object display image signal.

EXPLANATION OF REFERENCES

1, 41, 44: Ultrasonic wave device
2,47A: Array transducer
3: Transmitter
4: Receiver
5: Data separator
6, 49: Tomographic image signal generator
7: Image superposing unit
8: Display controller
9: Display
10: Insertion object image signal generator
11: First signal width detector
12, 34, 37: Insertion object display image signal generator
13: Insertion object
13A: Cable
13B: Connector
14: Insertion object laser light source
15: Device controller
16: Operating unit
17: Storage
18: Probe
19, 43, 43A, 50: Processor
20: Light guide member
21: Photoacoustic wave generator
22: Laser rod
23: Excitation light source
24, 25: Mirror
26: Q switch
29: Amplifier
30: AD converter
31: Signal processing unit
32: DSC
33: Image processing unit
35: Insertion object image signal magnifier
36: Insertion object display image signal specifier
38: Image highlighting unit 42, 42A: Second signal width setting unit
45: Distal end diameter reader
46: Photoacoustic wave device
47: Probe
47B: Subject laser beam irradiator
48: Subject laser light source
A, FE: Distal end portion
B1: Subject beam irradiator
B2: Reception signal generator
C: Outline image signal
CT1, CT2: Outer peripheral portion
DC1, DC2: Display color
DR1, DR2: Display region
DW: Display width
E, PE: Signal strength
FL: Thin line
P0: Peak position
SA: Insertion object image signal
SB: Insertion object display image signal
SC: Enlarged image signal
T1, T2: Image of distal end portion of insertion object
U: Tomographic image
W1: First signal width
W2: Second signal width
W3: Third signal width

What is claimed is:

1. An acoustic wave device comprising:
a probe;
a processor that irradiates inside of a subject with an ultrasonic beam or laser beam from the probe;
an insertion object that is capable of being inserted into the subject and has a photoacoustic wave generator at a distal end portion;
an insertion object laser light source that generates a photoacoustic wave from the photoacoustic wave generator by irradiating the photoacoustic wave generator of the insertion object with laser beam; and
a display,
wherein the processor is configured to
receive an acoustic wave emitted from a tissue of the subject to generate a tomographic image generating reception signal by irradiating the inside of the subject with the ultrasonic beam or the laser beam from the probe, and receive a photoacoustic wave by the photoacoustic wave generator to generate an insertion object image generating reception signal,
generate a tomographic image signal representing a tomographic image of the subject from the tomographic image generating reception signal,
generate an insertion object image signal representing an image of the distal end portion of the insertion object from the insertion object image generating reception signal,
detect a first signal width of the insertion object image signal having a signal strength of a predetermined ratio to a peak value of a signal strength in the insertion object image signal,
generate, in a case where the first signal width is larger than a predetermined second signal width, an insertion object display image signal having a center at a peak position where the signal strength of the insertion object image signal becomes the peak value and having a maximum width corresponding to the second signal width from the insertion object image signal, and
generate, in a case where the first signal width is smaller than the second signal width, an insertion object display image signal having the center at the peak position and having a maximum width smaller than the second signal width from the insertion object image signal, and
superimpose the tomographic image of the subject and the image of the distal end portion of the insertion object to be displayed on the display on the basis of the tomographic image signal and the insertion object display image signal.

2. The acoustic wave device according to claim 1, wherein in a case where the first signal width is larger than the second signal width, the processor is further configured to generate the insertion object display image signal having the center at the peak position and formed by a portion ranging from the center to the second signal width, in the insertion object image signal.

3. The acoustic wave device according to claim 1, wherein in a case where the first signal width is smaller than the second signal width, the processor is further configured to generate the insertion object display image signal having the center at the peak position and formed by a portion ranging from the center to the first signal width, in the insertion object image signal.

4. The acoustic wave device according to claim 1, wherein in a case where the first signal width is smaller than a third signal width predetermined as a value smaller than the second signal width, the processor is further configured to generate the insertion object display image signal having a center at the peak position and having a maximum width corresponding to the third signal width.

5. The acoustic wave device according to claim 4, wherein the processor is further configured to generate an enlarged image signal obtained by enlarging the insertion object image signal until the signal width having the signal strength of the predetermined ratio to the peak value becomes larger than the third signal width, and generate a portion having a center at the peak position and ranging from the center to the third signal width, in the enlarged image signal, as the insertion object display image signal.

6. The acoustic wave device according to claim 5, wherein the enlarged image signal is an image signal obtained by increasing the signal strength of at least the portion having the center at the peak position and ranging from the center to the third signal width in the insertion object image signal at a predetermined magnification.

7. The acoustic wave device according to claim 5, wherein the enlarged image signal is an image signal obtained by enlarging a signal width of at least a portion including a signal strength larger than the signal strength of the predetermined ratio to the peak value in the insertion object image signal at a predetermined magnification.

8. The acoustic wave device according to claim 5, wherein the enlarged image signal is an image signal obtained by increasing a signal strength of at least the portion having the center at the peak position and ranging from the center to the third signal width in the insertion object image signal by a predetermined offset amount.

9. The acoustic wave device according to claim 5, wherein the enlarged image signal is an image signal obtained by increasing a signal strength of at least a portion smaller than a predetermined signal strength, in the portion having the center at the peak position and ranging from the center to the third signal width in the insertion object image signal, up to the predetermined signal strength.

10. The acoustic wave device according to claim 5, wherein the enlarged image signal is an image signal obtained by increasing a signal strength of at least the portion having the center at the peak position and ranging from the center to the third signal width in the insertion object image signal up to the peak value.

11. The acoustic wave device according to claim 1, wherein the processor is further configured to highlight and display the image of the distal end portion of the insertion object on the display in a case where the maximum width of the insertion object display image signal is different from the first signal width.

12. The acoustic wave device according to claim 11, wherein the processor is further configured to superimpose an outline of a region having a center at the peak position and having the first signal width and the image of the distal end portion of the insertion object to be displayed on the display.

13. The acoustic wave device according to claim 11, wherein the processor is further configured to display an outer peripheral portion of the image of the distal end portion of the insertion object in different colors on the display between a case where the maximum width of the insertion object display image signal is larger than the first signal width and a case where the maximum width of the insertion object display image signal is smaller than the first signal width.

14. The acoustic wave device according to claim 11, wherein the processor is further configured to display the image of the distal end portion of the insertion object in different colors on the display between a case where the maximum width of the insertion object display image signal is the first signal width and a case where the maximum width of the insertion object display image signal is different from the first signal width.

15. The acoustic wave device according to claim 14, wherein the processor is further configured to display the image of the distal end portion of the insertion object in different colors on the display between a case where the maximum width of the insertion object display image signal is larger than the first signal width and a case where the maximum width of the insertion object display image signal is smaller than the first signal width.

16. The acoustic wave device according to claim 1, further comprising:
an interface through which a user performs an input operation,
wherein the processor is further configured to set the second signal width, and
set a value set by the user through the interface as the second signal width.

17. The acoustic wave device according to claim 1, further comprising:
a distal end diameter reader that reads a diameter of the distal end portion of the insertion object,
wherein the processor is further configured to set the second signal width, and
calculate a converted value by multiplying the diameter of the distal end portion of the insertion object read by the distal end diameter reader by a predetermined coefficient, and set the converted value as the second signal width.

18. The acoustic wave device according to claim 1, wherein the processor is further configured to set the second signal width, and
set the second signal width on the basis of the first signal width detected in a calibration medium.

19. The acoustic wave device according to claim 1, wherein the probe irradiates the inside of the subject with an ultrasonic beam to cause an ultrasonic echo to be emitted from the tissue of the subject, and
wherein the processor is further configured to receive the ultrasonic echo from the tissue of the subject to generate the tomographic image generating signal.

20. The acoustic wave device according to claim 1, wherein the insertion object laser light source irradiates the inside of the subject with laser beam to cause the photoacoustic wave to be emitted from the tissue of the subject, and
wherein the processor is further configured to receive the photoacoustic wave from the tissue of the subject to generate the tomographic image generating reception signal.

21. A control method of an acoustic wave device, the method comprising:
receiving an acoustic wave emitted from a tissue of a subject by irradiating an inside of the subject with an ultrasonic beam or laser beam to generate a tomographic image generating reception signal;
irradiating a photoacoustic wave generator of an insertion object with the laser beam, the insertion object being able to be inserted into the subject and having the photoacoustic wave generator at a distal end portion;
receiving a photoacoustic wave from the photoacoustic wave generator to generate an insertion object image generating reception signal;
generating an insertion object image signal representing an image of the distal end portion of the insertion object from the insertion object image generating reception signal,
generating a tomographic image signal representing a tomographic image of the subject from the tomographic image generating reception signal,
detecting a first signal width of the insertion object image signal having a signal strength of a predetermined ratio to a peak value of a signal strength in the insertion object image signal,
generating, in a case where the first signal width is larger than a predetermined second signal width, an insertion object display image signal having a center at a peak position where the signal strength of the insertion object image becomes the peak value and having a maximum width corresponding to the second signal width, from the insertion object image signal;
generating, in a case where the first signal width is smaller than the second signal width, an insertion object display image signal having a center at the peak position and having a maximum width smaller than the second signal width; and
superimposing a tomographic image of the subject and an image of the distal end portion of the insertion object to be displayed on a display on the basis of the tomographic image signal and the insertion object display image signal.

* * * * *